(12) United States Patent
Babkin et al.

(10) Patent No.: US 11,051,867 B2
(45) Date of Patent: Jul. 6, 2021

(54) TISSUE CONTACT VERIFICATION SYSTEM

(71) Applicant: ADAGIO MEDICAL, Inc., Laguna Hills, CA (US)

(72) Inventors: Alexei Babkin, Dana Point, CA (US); Meital Mazor, Laguna Hills, CA (US); Larry Varnado, Laguna Hills, CA (US)

(73) Assignee: Adagio Medical, Inc., Laguna Hills, CA (US)

( * ) Notice: Subject to any disclaimer, the term of this patent is extended or adjusted under 35 U.S.C. 154(b) by 331 days.

(21) Appl. No.: 15/755,523

(22) PCT Filed: Sep. 15, 2016

(86) PCT No.: PCT/US2016/051954
§ 371 (c)(1),
(2) Date: Jun. 13, 2018

(87) PCT Pub. No.: WO2017/048965
PCT Pub. Date: Mar. 23, 2017

(65) Prior Publication Data
US 2019/0125422 A1 May 2, 2019

Related U.S. Application Data

(60) Provisional application No. 62/220,425, filed on Sep. 18, 2015.

(51) Int. Cl.
*A61B 18/12* (2006.01)
*A61B 18/02* (2006.01)
(Continued)

(52) U.S. Cl.
CPC .... *A61B 18/02* (2013.01); *A61B 2017/00044* (2013.01); *A61B 2018/00351* (2013.01);
(Continued)

(58) Field of Classification Search
CPC .......... A61B 18/02; A61B 2018/00351; A61B 2018/00577; A61B 2018/00642;
(Continued)

(56) References Cited

U.S. PATENT DOCUMENTS 34,502 A 2/1862 Johnson et al.
3,062,017 A 11/1962 Balcar
(Continued)

FOREIGN PATENT DOCUMENTS

GB 1422535 1/1976
GB 2283678 6/1996
(Continued)

OTHER PUBLICATIONS

Supplementary European Search Report dated Apr. 5, 2019 of the counterpart application EP16847307.2.
(Continued)

*Primary Examiner* — Daniel W Fowler
(74) *Attorney, Agent, or Firm* — Richard Batt

(57) ABSTRACT

A system for monitoring electrical activity at an ablation site where the system includes an ablation device having an elongate, flexible shaft and a distal treatment section for delivering ablation energy to target tissue, a first electrode mounted on the distal treatment section, a second electrode mounted on the distal treatment section where the second electrode is spaced from the first electrode a distance (D1), a plurality of conducting elements extending along the distal treatment section and being connected to the first electrode and the second electrode, the plurality of conducting elements for connecting the first electrode and the second electrode to an electrophysiological recording system, a processing device programmed to receive the electrical
(Continued)

information from the ablation site from the first electrode and the second electrode, and an electrophysiological recording system.

17 Claims, 8 Drawing Sheets

(51) Int. Cl.
    *A61B 18/00*         (2006.01)
    *A61B 17/00*         (2006.01)
    *A61B 90/00*         (2016.01)

(52) U.S. Cl.
    CPC ............... *A61B 2018/00577* (2013.01); *A61B 2018/00642* (2013.01); *A61B 2018/00744* (2013.01); *A61B 2018/00791* (2013.01); *A61B 2018/00839* (2013.01); *A61B 2018/00875* (2013.01); *A61B 2018/0212* (2013.01); *A61B 2018/0262* (2013.01); *A61B 2090/065* (2016.02)

(58) Field of Classification Search
    CPC ........... A61B 2018/00744; A61B 2018/00791; A61B 2018/00839; A61B 2018/00875; A61B 2018/0212; A61B 2018/1262; A61B 2017/00044; A61B 2090/065
    See application file for complete search history.

(56) References Cited

U.S. PATENT DOCUMENTS

| | | | |
|---|---|---|---|
| 3,613,689 A | 10/1971 | Crump |
| 3,889,680 A | 6/1975 | Arrnao |
| 3,942,010 A | 3/1976 | Peterson |
| 3,993,123 A | 11/1976 | Chu |
| 4,034,251 A | 7/1977 | Haas |
| 4,167,771 A | 9/1979 | Simons |
| 4,226,281 A | 10/1980 | Chu |
| 4,281,268 A | 7/1981 | Sawa |
| 4,384,360 A | 5/1983 | Kitadate |
| 4,418,421 A | 11/1983 | Klitadate |
| 4,519,389 A | 5/1985 | Gudkin |
| 4,548,045 A | 10/1985 | Altares |
| 4,802,475 A | 2/1989 | Weshahy |
| 4,838,041 A | 6/1989 | Bellows |
| 4,843,446 A | 6/1989 | Nishino |
| 4,945,562 A | 7/1990 | Staub |
| 4,946,460 A | 8/1990 | Merry |
| 4,982,080 A | 1/1991 | Wilson |
| 5,012,505 A | 4/1991 | Zupancic |
| 5,037,395 A | 8/1991 | Spencer |
| 5,108,390 A | 4/1992 | Potocky |
| 5,147,355 A | 9/1992 | Friedman |
| 5,147,538 A | 9/1992 | Wright |
| 5,155,093 A | 10/1992 | Den |
| 5,173,606 A | 12/1992 | Weinberger |
| 5,211,646 A | 5/1993 | Alperovich |
| 5,212,626 A | 5/1993 | Bell |
| 5,214,925 A | 6/1993 | Hoy |
| 5,237,824 A | 8/1993 | Pawliszyn |
| 5,254,116 A | 10/1993 | Baust |
| 5,274,237 A | 12/1993 | Gallagher |
| 5,275,595 A | 1/1994 | Dobak, III |
| 5,324,286 A | 6/1994 | Fowle |
| 5,334,181 A | 8/1994 | Rubinsky |
| 5,369,384 A | 11/1994 | Woods |
| 5,400,602 A | 3/1995 | Chang |
| 5,405,533 A | 4/1995 | Hazleback |
| 5,417,072 A | 5/1995 | Sliver |
| 5,433,717 A | 7/1995 | Rubinsky |
| 5,452,582 A | 9/1995 | Longsworth |
| 5,462,544 A * | 10/1995 | Saksena ............... A61B 5/0422 606/15 |
| 5,471,844 A | 12/1995 | Levi |
| 5,494,039 A | 2/1996 | Onik |
| 5,504,924 A | 4/1996 | Ohashi |
| 5,520,682 A | 5/1996 | Baust |
| 5,531,742 A | 7/1996 | Barken |
| 5,573,532 A | 11/1996 | Chang |
| 5,603,221 A | 2/1997 | Maytal |
| 5,661,980 A | 9/1997 | Gallivan |
| 5,702,435 A | 12/1997 | Maytal |
| 5,716,353 A | 2/1998 | Matsura |
| 5,733,280 A | 3/1998 | Avitall |
| 5,741,248 A | 4/1998 | Stern |
| 5,757,885 A | 5/1998 | Yao |
| 5,800,487 A | 9/1998 | Mikus |
| 5,800,488 A | 9/1998 | Crockett |
| 5,816,052 A | 10/1998 | Foote |
| 5,885,276 A | 3/1999 | Ammar |
| 5,899,897 A | 5/1999 | Rabin |
| 5,899,898 A | 5/1999 | Arless |
| 5,899,899 A | 5/1999 | Arless |
| 5,901,783 A | 5/1999 | Dobak, III |
| 5,910,104 A | 6/1999 | Dobak, III |
| 5,916,212 A | 6/1999 | Baust |
| 5,924,975 A | 7/1999 | Goldowsky |
| 5,947,960 A | 9/1999 | Griswold |
| 5,950,444 A | 9/1999 | Matsunaga |
| 5,957,963 A | 9/1999 | Dobak |
| 5,978,697 A | 11/1999 | Maytal |
| 5,993,444 A | 11/1999 | Ammar |
| 5,997,781 A | 12/1999 | Nishikawa |
| 6,004,269 A | 12/1999 | Crowley |
| 6,039,730 A | 3/2000 | Rabin |
| 6,074,412 A | 6/2000 | Mikus |
| 6,096,068 A | 8/2000 | Dobak |
| 6,106,518 A | 8/2000 | Wittenberger |
| 6,139,544 A | 10/2000 | Mikus |
| 6,142,991 A | 11/2000 | Schatzberger |
| 6,161,543 A | 12/2000 | Cox |
| 6,171,277 B1 | 1/2001 | Ponzi |
| 6,179,831 B1 | 1/2001 | Bliweis |
| 6,182,666 B1 | 2/2001 | Dobak, III |
| 6,190,378 B1 | 2/2001 | Jarvinen |
| 6,190,382 B1 | 2/2001 | Ormsby |
| 6,193,644 B1 | 2/2001 | Dobak, III |
| 6,198,974 B1 | 3/2001 | Webster |
| 6,235,018 B1 * | 5/2001 | LePivert ............... A61B 18/02 600/547 |
| 6,237,355 B1 | 5/2001 | Li |
| 6,241,722 B1 | 6/2001 | Dobak |
| 6,251,105 B1 | 6/2001 | Mikus |
| 6,263,046 B1 | 7/2001 | Rogers |
| 6,270,493 B1 | 8/2001 | Lalonde |
| 6,307,916 B1 | 10/2001 | Rogers |
| 6,324,852 B1 | 12/2001 | Cheng |
| 6,341,629 B1 | 1/2002 | Clark |
| 6,347,675 B1 | 2/2002 | Kolle |
| 6,355,029 B1 | 3/2002 | Joye |
| 6,368,304 B1 | 4/2002 | Aliberto |
| 6,377,659 B1 | 4/2002 | Snyder |
| 6,396,901 B1 | 5/2002 | Heil |
| 6,432,174 B1 | 6/2002 | Heung |
| 6,440,126 B1 | 8/2002 | Abboud |
| 6,451,011 B2 | 9/2002 | Tu |
| 6,471,694 B1 | 10/2002 | Kudaravalli |
| 6,475,212 B2 | 11/2002 | Dobak |
| 6,477,231 B2 | 11/2002 | Snyder |
| 6,486,078 B1 | 11/2002 | Rangarajan |
| 6,520,933 B1 | 2/2003 | Evans |
| 6,527,765 B2 | 3/2003 | Kelman |
| 6,530,420 B1 | 3/2003 | Takada |
| 6,537,271 B1 | 3/2003 | Murray |
| 6,544,176 B2 | 4/2003 | Mikus |
| 6,551,309 B1 | 4/2003 | LePivert |
| 6,554,797 B1 | 4/2003 | Worthen |
| 6,572,610 B2 | 6/2003 | Kovalcheck |
| 6,584,332 B2 | 6/2003 | Yoshitake |
| 6,592,581 B2 | 7/2003 | Bowe |
| 6,602,276 B2 | 8/2003 | Dobak, III |
| 6,622,494 B1 | 9/2003 | Pourrahimi |

(56) References Cited

U.S. PATENT DOCUMENTS

| | | |
|---|---|---|
| 6,622,507 B2 | 9/2003 | Cotte |
| 6,628,002 B2 | 9/2003 | Ritz |
| 6,648,879 B2 | 11/2003 | Joye |
| 6,685,720 B1 | 2/2004 | Wu |
| 6,706,037 B2 | 3/2004 | Zvuloni |
| 6,726,653 B2 | 4/2004 | Noda |
| 6,737,225 B2 | 5/2004 | Miller |
| 6,746,445 B2 | 6/2004 | Abboud |
| 6,767,346 B2 | 7/2004 | Damasco |
| 6,771,996 B2 | 8/2004 | Bowe et al. |
| 6,812,464 B1 | 11/2004 | Sobolewski |
| 6,848,502 B2 | 1/2005 | Bishop |
| 6,848,458 B1 | 2/2005 | Shrinivasan |
| 6,893,419 B2 | 5/2005 | Noda |
| 6,893,433 B2 | 5/2005 | Lentz |
| 6,905,492 B2 | 6/2005 | Zvuloni |
| 6,905,493 B2 | 6/2005 | Lentz |
| 6,936,045 B2 | 6/2005 | Yu |
| 6,941,953 B2 | 9/2005 | Feld |
| 6,989,009 B2 | 1/2006 | Lafontaine |
| 7,004,937 B2 | 2/2006 | Lentz |
| 7,013,170 B2 | 3/2006 | Bowe |
| 7,022,120 B2 | 4/2006 | Lafontaine |
| 7,083,612 B2 | 8/2006 | Littrup |
| 7,110,506 B2 | 9/2006 | Radley |
| 7,160,290 B2 | 1/2007 | Eberl |
| 7,220,252 B2 | 5/2007 | Shah |
| 7,220,257 B1 | 5/2007 | Lafontaine |
| 7,195,625 B2 | 7/2007 | Lentz |
| 7,258,161 B2 | 8/2007 | Cosley et al. |
| 7,273,479 B2 | 9/2007 | Littrup et al. |
| 7,410,484 B2 | 8/2008 | Littrup et al. |
| 7,648,497 B2 | 1/2010 | Lane et al. |
| 7,740,627 B2 | 6/2010 | Gammie et al. |
| 7,842,031 B2 | 11/2010 | Abboud et al. |
| 8,012,147 B2 | 9/2011 | Lafontaine |
| 8,177,780 B2 | 5/2012 | Cox |
| 8,298,217 B2 | 10/2012 | Lane |
| 8,387,402 B2 | 3/2013 | Littrup |
| 8,475,441 B2 | 7/2013 | Babkin |
| 8,641,704 B2 | 2/2014 | Werneth |
| 8,679,104 B2 | 3/2014 | Abboud et al. |
| 8,685,014 B2 | 4/2014 | Babkin |
| 8,740,891 B2 | 6/2014 | Babkin |
| 8,740,892 B2 | 6/2014 | Babkin |
| 8,845,628 B2 | 9/2014 | Babkin |
| 8,888,768 B2 | 11/2014 | Babkin |
| 8,945,106 B2 | 2/2015 | Arless |
| 9,095,320 B2 | 8/2015 | Littrup |
| 9,480,521 B2 | 11/2016 | Kim et al. |
| 10,159,521 B2 | 12/2018 | Jannicke et al. |
| 10,182,742 B2 | 1/2019 | Condie et al. |
| 10,194,978 B2 | 2/2019 | Coulombe |
| 10,271,899 B2 | 4/2019 | Deac |
| 10,405,919 B2 | 9/2019 | Fung et al. |
| 2001/0024485 A1 | 9/2001 | Rogers |
| 2001/0047134 A1 | 11/2001 | Holdaway |
| 2002/0007180 A1* | 1/2002 | Wittenberger ......... A61B 18/02 |
| | | 606/21 |
| 2002/0049409 A1 | 4/2002 | Noda |
| 2002/0062831 A1 | 5/2002 | Beyar |
| 2002/0072741 A1 | 6/2002 | Sliwa |
| 2002/0087152 A1 | 7/2002 | Mikus |
| 2002/0151331 A1 | 10/2002 | Abdelmonem |
| 2003/0040740 A1 | 2/2003 | Kovalcheck |
| 2003/0055415 A1 | 3/2003 | Yu |
| 2003/0060815 A1* | 3/2003 | Lalonde ................ A61B 18/02 |
| | | 606/23 |
| 2003/0195605 A1 | 10/2003 | Kovalcheck |
| 2003/0199817 A1 | 10/2003 | Thompson |
| 2004/0027462 A1 | 2/2004 | Hing |
| 2004/0118144 A1 | 6/2004 | Hsu |
| 2004/0148004 A1 | 7/2004 | Wallsten |
| 2004/0215295 A1 | 10/2004 | Littrup |
| 2005/0027289 A1 | 2/2005 | Castellano |
| 2005/0070887 A1* | 3/2005 | Taimisto ............ A61B 18/1492 |
| | | 606/41 |
| 2005/0159788 A1* | 7/2005 | Kress ..................... A61B 5/042 |
| | | 607/32 |
| 2005/0209587 A1 | 9/2005 | Joye |
| 2005/0261573 A1 | 11/2005 | Littrup |
| 2006/0235375 A1 | 6/2006 | Littrup |
| 2006/0212028 A1 | 9/2006 | Joye |
| 2006/0235357 A1 | 10/2006 | Littrup |
| 2006/0247611 A1 | 11/2006 | Abboud |
| 2006/0253114 A1 | 11/2006 | Saadat |
| 2007/0062547 A1* | 3/2007 | Pappone ................ A61B 34/70 |
| | | 128/898 |
| 2007/0255162 A1* | 11/2007 | Abboud ................ A61B 5/0537 |
| | | 600/547 |
| 2007/0299432 A1 | 12/2007 | Arless et al. |
| 2008/0119836 A1 | 5/2008 | Littrup |
| 2008/0312644 A1 | 12/2008 | Fourkas |
| 2009/0118723 A1 | 5/2009 | Lalonde |
| 2009/0177111 A1* | 7/2009 | Miller ..................... A61B 5/053 |
| | | 600/547 |
| 2009/0182316 A1* | 7/2009 | Bencini ................. A61B 18/02 |
| | | 606/21 |
| 2009/0281541 A1* | 11/2009 | Ibrahim ............. A61B 18/1492 |
| | | 606/42 |
| 2010/0057063 A1 | 3/2010 | Adess |
| 2010/0256621 A1 | 10/2010 | Babkn |
| 2011/0009854 A1 | 1/2011 | Babkin |
| 2011/0040297 A1 | 2/2011 | Babkn |
| 2011/0054453 A1 | 3/2011 | Lalonde |
| 2011/0162390 A1 | 7/2011 | Littrup |
| 2011/0184399 A1 | 7/2011 | Wittenberger |
| 2012/0059364 A1 | 3/2012 | Baust |
| 2012/0109118 A1 | 5/2012 | Lalonde |
| 2012/0253336 A1 | 10/2012 | Littrup |
| 2013/0073014 A1 | 3/2013 | Lim |
| 2013/0085416 A1* | 4/2013 | Mest ....................... G01L 25/00 |
| | | 600/587 |
| 2013/0110098 A1* | 5/2013 | Lalonde ................ A61B 18/02 |
| | | 606/21 |
| 2013/0197498 A1 | 8/2013 | Laske |
| 2013/0324987 A1 | 12/2013 | Leung |
| 2013/0331829 A1 | 12/2013 | Babkin |
| 2013/0345688 A1 | 12/2013 | Babkn |
| 2014/0364848 A1 | 12/2014 | Heimbecher |
| 2015/0018809 A1 | 1/2015 | Mihalik |
| 2015/0250524 A1 | 9/2015 | Moriarty |
| 2019/0038171 A1 | 2/2019 | Howard |
| 2019/0254735 A1 | 8/2019 | Stewart et al. |
| 2019/0262056 A1 | 8/2019 | Yang et al. |
| 2019/0357959 A1 | 11/2019 | Hou et al. |

FOREIGN PATENT DOCUMENTS

| | | |
|---|---|---|
| JP | 7-136180 | 5/1995 |
| JP | 2008-515469 | 5/2008 |
| WO | WO1993008751 | 5/1993 |
| WO | WO1997049344 | 12/1997 |
| WO | WO2002058576 | 8/2002 |
| WO | WO2002096270 | 12/2002 |
| WO | WO2002011638 | 4/2003 |
| WO | 2004/064914 | 8/2004 |
| WO | WO2004064914 | 3/2005 |
| WO | WO2006137887 | 12/2006 |
| WO | 2009/009398 | 1/2009 |
| WO | WO2009067497 | 5/2009 |
| WO | WO2013013098 | 1/2013 |
| WO | WO2013013099 | 1/2013 |
| WO | WO2015057450 | 4/2015 |
| WO | WO2015160574 | 10/2015 |

OTHER PUBLICATIONS

Office Action dated Jul. 26, 2018 for U.S. Appl. No. 14/915,631.
Office Action dated Jul. 13, 2018 for U.S. Appl. No. 15/028,925.
Supplemental European Search Report dated Apr. 23, 2018 for EP15858716.

(56) References Cited

OTHER PUBLICATIONS

Australian Examination Report No. 1, dated Jul. 31, 2018 for 2014327045.
Arai, Y., et al., "Supercritical Fluids," pp. 161 and 199, ISBN 3540412484, Springer 2002.
Barron, Randall F., "Cryogenic Heat Transfer," pp. 97, 129 and 130, Taylor & Francis, 1999.
Bunch TJ, Cutler MJ. Is pulmonary vein isolation still the cornerstone in atrial fibrillation ablation? J Thorac Dis. Feb. 2015;7(2):132-41.
Callans DJ, Gerstenfeld EP, Dixit S, et al. Efficacy of repeat pulmonary vein isolation procedures in patients with recurrent atrial fibrillation. J Cardiovasc Electrophysiol 2004;15:1050-5.
Kim et al. Linear ablation in addition to circumferential pulmonary vein isolation (Dallas lesion set) does not improve clinical outcome in patients with paroxysmal atrial fibrillation: a prospective randomized study. Europace. Mar. 2015;17(3):388-95.
Kowalski M, Grimes MM, Perez FJ, et al. Histopathologic characterization of chronic radiofrequency ablation lesions for pulmonary vein isolation. J Am Coll Cardiol 2012;59;930-8.
Lide, D.R, and Keihiaian, H.V., "CRC Handbook of Thermophysical and Thermochemical Data," p. 375, CRC Press 1994.
McGann CJ, Kholmovski EG, Oakes RS, et al. New magnetic resonance imaging-based method for defining the extent of left atrial wall injury after the ablation of atrial fibrillation, J Am Coll Cardiol 2008;52:1263-71.
Ranjan R, Kato R, Zviman MM, et al. Gaps in the ablation line as a potential cause of recovery from electrical isolation and their visualization using MRI. Circ Arrhythm Electrophysiol 2011;4:279-86.
Ouyang F, Tilz R, Chun J, et al. Long-term results of catheter ablation in paroxysmal atrial fibrillation: lessons from a 5-year follow-up. Circulation 2010;122:2368-77.
Sawriney N; Anousheh R, Chen WC, et al. Five-year outcomes after segmental pulmonary vein isolation for paroxysmal atrial fibrillation. Am J Cardiol 2009;104:366-72.
Sun, Ya-ping, Supercritical Fluid Technology in Materials Science and Engineering, pp. 1 and 26, CRC Press 2002.
Thakore, S.B. and Bhatt, B.I., "Introduction to Process Engineering and Design," Chemical Engineering Series, pp. 27-28, McGraw-Hill 2008.
Verna A, Kilicaslan F, Pisano E, et al. Response of atrial fibrillation to pulmonary vein antrum isolation is directly related to resumption and delay of pulmonary vein conduction. Circulation 2005;112:627-35.
Stuehlinger, M., et al,, "CoolLoop First: A First in Man Study to Test a Novel Circular Cryoablation System in Paroxysmal Artial Fibrillation," Journal of Artial Fibrillation, vol. 81, Issue 3, Oct.-Nov. 2015.
Skanes, Allan C., et al., "Cryoblation: Potentials and Pitfalls," doi:10.1046/j.1540-8167.2004.15106.x, Jul. 6, 2004.
Lemola, Kristina, MD, et al., "Pulmonary Vein Isolation as an End Point for Left Atrial Circumferential Ablation of Atrial Fibrillaton," Journal of American College of Cardiology, vol. 46, No. 6, 2005.
Rolf, Sascha, MD, et al., "Electroanatomical Mapping of Atrial Fibrillation: Review of the Current Techniques and Advances," Journal of Artrial Fibrillation, vol. 7, Issue 4, Dec. 2014-Jan. 2015.
International Search Report dated Mar. 18, 2015 for PCT/US14/56839.
International Search Report dated Jan. 21, 2015 for PCT/US2014/059684.
International Search Report dated Oct. 1, 2012 for PCT/US2012/047487.
International Search Report /Written Opinion dated Jan. 14, 2009 for PCT/US2008/084004.
International Preliminary Examination Report dated Oct. 18, 2016 for PCT/US2015/024778.
European Search Report for EP04702597 dated Sep. 18, 2007.
European Search Report for EP08852254 dated Nov. 19, 2010.
European Search Report for EP05858178.6 dated Nov. 5, 2010.
European Search Report for EP10184565 dated Feb. 21, 2011.
International Search Report dated Jul. 8, 2015 for PCT/US2015/024778.
International Search Report dated Dec. 28, 2016. for PCT/US2016/033833.
International Search Report dated Jan. 31, 2017 for PCT/US2016/051954.
International Search Report dated Feb. 2, 2017 for PCT/US2016/063882.
International Search Report dated Jan. 15, 2016 for PCT/US2015/056780.

\* cited by examiner

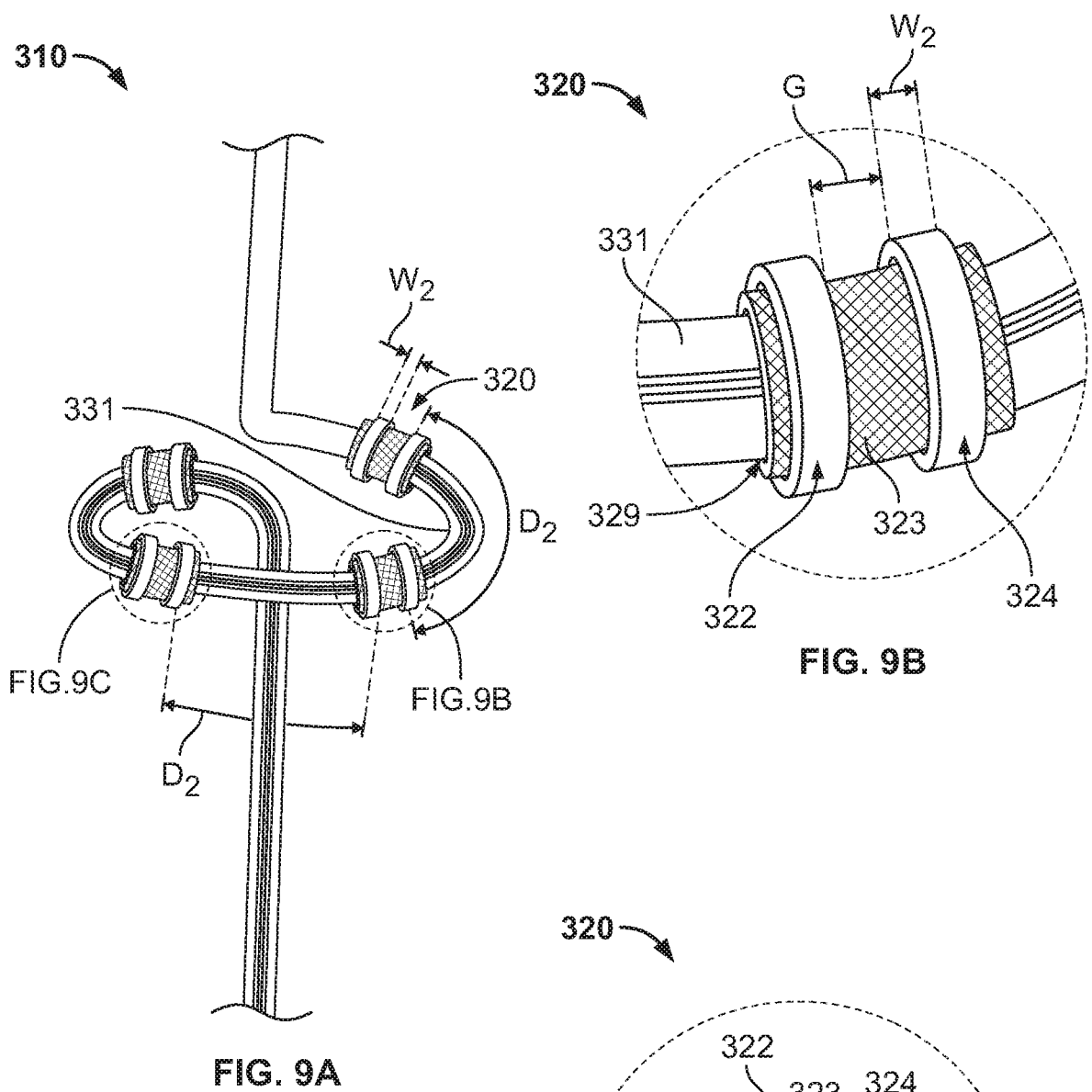
FIG. 9A
FIG. 9B
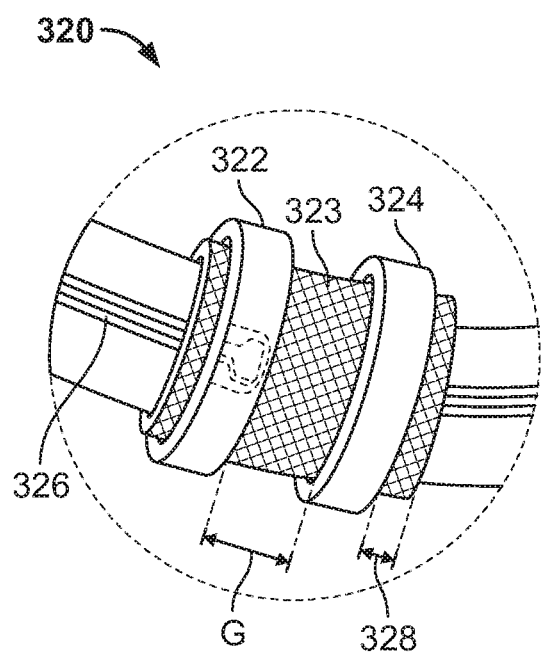
FIG. 9C

TISSUE CONTACT VERIFICATION SYSTEM

CROSS-REFERENCE TO RELATED APPLICATIONS

This application is a national phase filing under 35 U.S.C. 371 of International Patent Application No. PCT/US2016/051954, filed Sep. 15, 2016, which claims the benefit of U.S. Provisional Application No. 62/220,425, filed Sep. 18, 2015, the entire contents of which are incorporated herein by reference.

BACKGROUND

1. Field of the Invention

Embodiments of the present invention relate to cryosurgery and more particularly to cryoablation systems adapted to confirm contact between a freeze section of the cryoablation catheter and the target tissue to be ablated/frozen.

2. Description of the Related Art

Cryoablation is a surgical technique for ablating tissue by cooling or freezing the tissue to a lethal degree. Cryoablation has the benefit of minimizing permanent collateral tissue damage and has applicability to a wide range of therapies including the treatment of heart disease.

Atrial flutter is a condition where the atria beat very quickly, but still evenly. Atrial fibrillation is not an uncommon form of heart disease. Atrial fibrillation occurs when anatomical obstacles in the heart disrupt the normally uniform propagation of electrical impulses in the atria. These anatomical obstacles (or conduction blocks) can cause the electrical impulse to degenerate into several circular wavelets that circulate about the obstacles. These wavelets, called "reentry circuits," disrupt the normally uniform activation of the left and right atria.

Because of a loss of atrioventricular synchrony, people who suffer from atrial fibrillation and atrial flutter also suffer the consequences of impaired hemodynamics and loss of cardiac efficiency. These people are also at greater risk of stroke and other thromboembolic complications because of loss of effective contraction and atrial stasis.

One surgical method of treating atrial fibrillation by interrupting pathways for reentry circuits is the so-called "maze procedure," which relies on a prescribed pattern of incisions to anatomically create a convoluted path, or maze, for electrical propagation within the left and right atria. The incisions direct the electrical impulse from the sinoatrial (SA) node along a specified route through all regions of both atria, causing uniform contraction required for normal atrial transport function. The incisions finally direct the impulse to the atrioventricular (AV) node to activate the ventricles, restoring normal atrioventricular synchrony. The incisions are also carefully placed to interrupt the conduction routes of the most common reentry circuits. The maze procedure has been found effective in treating atrial fibrillation. However, the maze procedure is technically difficult to perform. It also requires open heart surgery and use of a heart-lung machine, all of which is very expensive.

Maze-like procedures have also been developed utilizing energy sources to provide ablation energy to, for example, catheters, which can form lesions on the endocardium (the lesions being 1 to 15 cm in length and of varying shape) to effectively create a maze for electrical conduction in a predetermined path. The formation of these lesions by soft tissue coagulation (or ablation) can provide the same therapeutic benefits that the complex incision patterns that the surgical maze procedure presently provides, but without invasive, open heart surgery.

One lesion that has proven to be difficult to form with conventional devices is the circumferential lesion that is used to isolate the pulmonary vein to cure ectopic atrial fibrillation. Lesions that isolate the pulmonary vein may be formed within the pulmonary vein itself or in the tissue surrounding the pulmonary vein. Ablation of pulmonary veins is currently performed by placing a diagnostic catheter (such as Biosense Webster's Lasso™ circular ECG catheter, Irvine Biomedical's Afocus™ circular ECG catheter, or Boston Scientific Corporation's Constellation™ ECG catheter) into the pulmonary vein to be treated, and then ablating the pulmonary tissue adjacent to the distal end of the selected diagnostic catheter with a standard, commercially-available ablation catheter. The diagnostic catheter is used to determine if the lesion created by the ablation catheter has been successful in electrically isolating the pulmonary vein.

Some physicians may alternatively use a standard linear diagnostic catheter with 2-20 ECG electrodes to evaluate pre-ablation electrocardiogram (ECG) recordings. The physician then swaps the diagnostic catheter with a standard ablation catheter either through the same sheath, or in conjunction with the ablation catheter through a second sheath, ablating the area surrounding the pulmonary veins. The physician then swaps the ablation catheter with the diagnostic catheter to evaluate post-ablation ECG recordings.

The circumferential lesion must be iteratively formed by placing the ablation electrode into contact with a tissue region, ablating the tissue region, moving the ablation electrode into contact with another tissue region, and then ablating again. In a standard procedure, placement of the electrode and ablation of tissue may be repeated from 15-25 times to create the circumferential lesion necessary to electrically isolate the tissue. It is often difficult to form an effective, continuous circumferential lesion from a pattern of relatively small diameter lesions.

More recently, inflatable balloon-like devices that can be expanded within or adjacent to the pulmonary vein have been introduced.

US Patent Publication No. 2015/0018809 to Mihalik, for example, describes a method and system for cryotreatment and mapping of target tissue. The cryotreatment system may include a cryotreatment catheter, a mapping catheter including one or more mapping electrodes, and one or more temperature sensors located on the mapping catheter and/or the cryotreatment catheter. The cryotreatment catheter distal tip may be short enough to allow at least one mapping electrode to be positioned proximate the cryoballoon. Energy, such as radiofrequency energy, may be delivered to one or more mapping electrodes when one or more temperature sensors indicate a temperature of approximately 0° C. or below at one or more mapping electrode in order to thaw or prevent the formation of ice on the mapping electrodes when positioned proximate a cryoballoon during a cryotreatment procedure in order to recapture cardiac signals.

Although the above mentioned devices can be used to create various shaped lesions with some of better quality than others, the step of confirming whether the cryoenergy delivery section is in contact with the target tissue is still an important problem to be solved. Failure to make good tissue contact results in poor thermal conduction, and less predictable results.

Confirming whether the cryoenergy device is in contact with the target tissue is problematic because the diagnostic monitoring electrodes are either 1) on a separate device, or 2) offset a distance from the energy delivery section of the catheter. Consequently, the surgeon still does not know whether the energy delivery section is firmly contacting the target tissue. The surgeon may only estimate tissue contact based on fluoroscopy views, and the electrophysiological (EP) data transmitted from electrodes positioned nearby (but not within) the freeze zone. This type of instrument positioning is not straightforward, even for experienced surgeons.

Accordingly, there remains a need for a system that more accurately determines/confirms tissue contact and position of a catheter or other ablation device during an ablation procedure.

SUMMARY

In embodiments, an endovascular cryoablation system for creating a lesion in tissue comprises a cryogen pressure source or generator; a cryogen cooler for cooling the cryogen; a cryoablation catheter in fluid communication with the generator; and a controller operable to control the cooling power delivered from a distal treatment section of the catheter to the tissue to cool the tissue. The catheter includes a distal treatment section and a plurality of electrodes thereon for receiving electrical information from the tissue before and after cooling the tissue. The electrical information is transmitted to a programmed processor to verify/confirm tissue contact, catheter positioning and/or procedure efficacy.

In embodiments, a cryoablation method for creating a lesion in tissue comprises: a) advancing a distal treatment section of a cryoablation catheter through the vasculature such that a continuous, elongate freeze surface of the catheter is located adjacent the tissue to be cooled; b) evaluating a position of the continuous, elongate freeze surface in direct contact with the tissue to be cooled; c) cooling the tissue by circulating a cryogenic fluid through the catheter; d) confirming cooling of the tissue at the elongate freeze surface during a freeze cycle; and e) confirming tissue necrosis of the target tissue.

In embodiments, the step of confirming tissue necrosis is performed without moving the continuous, elongate freeze surface.

In embodiments, the electrical information comprises ECG signals.

In embodiments, the electrical information comprises resistance or impedance information.

In embodiments, the method further comprises displaying a tissue contact value based on an evaluating step.

In embodiments, the method further comprises the step of indicating whether the cryoablation catheter is safe to move from the tissue following the step of freezing.

In embodiments, the advancing step advances the continuous elongate active freeze surface adjacent to the right or left pulmonary vein antrums, posterior wall of the left atrium or CTI (cavo-tricuspid isthmus).

In embodiments, the step of confirming tissue necrosis comprises monitoring and measuring electrical signals from the target tissue to determine the presence or absence of cardiac cell or other tissue potentials.

In embodiments, the step of confirming freezing is performed by confirming ice formation surrounding the continuous, elongate freeze surface.

In some embodiments, a system for monitoring electrical activity at an ablation site is disclosed. The system comprises an ablation device having a treatment section for delivering ablation energy for ablating tissue; a polymeric sleeve included on at least a portion of the treatment section; at least one electrode set disposed along the treatment section of the ablation device. The at least one electrode set includes (i) a first ring-shaped electrode that has a first width and which is mounted on the polymeric sleeve, and (ii) a second ring-shaped electrode that has a second width and which is mounted on the polymeric sleeve, where the second ring-shaped electrode is spaced from the first ring-shaped electrode a distance ($D_1$). The system also includes at least one conducting element extending along the treatment section and which is connected to each electrode in the at least one electrode set, where the at least one conducting element is for connecting the at least one electrode set to an electrophysiological recording system. In some embodiments, the system also includes a processing device programmed to receive the electrical information from the ablation site from the at least one electrode set and to interpret the received electrical information to determine treatment section tissue contact conditions at the ablation site.

Some embodiments of the present invention are directed to a system for monitoring and transmitting electrical information at an ablation site. In these embodiments, the system comprises an ablation device having a treatment section for delivering ablation energy for ablating tissue; a polymeric sleeve included on at least a portion of the treatment section; and a plurality of electrode sets disposed along the treatment section of the ablation device, where each electrode set includes (i) a first ring-shaped electrode that has a first width and which is mounted on the polymeric sleeve and (ii) a second ring-shaped electrode that has a second width and which is mounted on the polymeric sleeve, wherein the second ring-shaped electrode is spaced from the first ring-shaped electrode a distance ($D_1$). The system also comprises at least one conducting element extending along the treatment section that is connected to each electrode in each electrode set in the plurality of electrode sets where the at least one conducting element is for connecting the plurality of electrode sets to an electrophysiological recording system; a processing device programmed to receive the electrical information from the ablation site from the plurality of electrode sets and to interpret the received electrical information to determine treatment section tissue contact conditions at the ablation site; and an electrophysiological recording system.

In some embodiments, the present invention is directed to a system for monitoring electrical activity at an ablation site where the system comprises: an ablation device having an elongate, flexible shaft and a distal treatment section for delivering ablation energy to target tissue; a first electrode mounted on the distal treatment section; a second electrode mounted on the distal treatment section where the second electrode is spaced from the first electrode a distance ($D_1$); a plurality of conducting elements extending along the distal treatment section and being connected to the first electrode and the second electrode, the plurality of conducting elements for connecting the first electrode and the second electrode to an electrophysiological recording system; a processing device programmed to receive the electrical information from the ablation site from the first electrode and the second electrode; and an electrophysiological recording system. In some embodiments, the processing device is programmed to interpret the received electrical information to determine treatment section tissue contact conditions at the ablation site. In some embodiments, the ablation device is a cryoablation catheter.

In additional embodiments, the present invention is directed to an ablation device comprising: a handle; an elongate, flexible shaft having a distal treatment section for delivering ablation energy to target tissue; a plurality of electrode sets disposed along the distal treatment section, wherein each electrode set comprises (i) a first electrode mounted on the distal treatment section and having a first width and (ii) a second electrode mounted on the distal treatment section and having a second width, where the second electrode is spaced from the first electrode a distance ($D_1$); and a plurality of conducting elements extending along the distal treatment section and being connected to each electrode in each electrode set in the plurality of electrode sets. The plurality of conducting elements for connecting the plurality of electrode sets to an electrophysiological recording system. In some embodiments, the ablation device is a cryoablation catheter. In some embodiments, the plurality of electrode sets monitor electrical activity in the target tissue. In some embodiments, the first electrode and the second electrode are ring-shaped.

Additional embodiments of the present invention are directed to an ablation device comprising: a handle; an elongate, flexible shaft having a distal treatment section for delivering ablation energy to target tissue; a first electrode mounted on the distal treatment section; a second electrode mounted on the distal treatment section where the second electrode is spaced from the first electrode a distance ($D_1$); and a plurality of conducting elements extending along the distal treatment section and which are connected to the first electrode and the second electrode. The plurality of conducting elements are for connecting the first electrode and the second electrode to an electrophysiological recording system. The first and second electrodes monitor/measure electrical activity in the target tissue. In some embodiments, the first and second electrodes are ring-shaped. In some embodiments, the ablation device is a cryoablation catheter and the ablation energy is cryoablation energy for freezing tissue.

BRIEF DESCRIPTION OF THE DRAWINGS

The description, objects and advantages of the embodiments of the present invention will become apparent from the detailed description to follow, together with the accompanying drawings.

FIG. 9A is a partial view of a cryoablation catheter comprising a plurality of electrode sets, according to an embodiment of the present invention;

FIG. 9B is an enlarged view of an electrode set shown in FIG. 9A, according to an embodiment of the present invention;

FIG. 9C is an enlarged view of another electrode set shown in FIG. 9A, according to an embodiment of the present invention;

DETAILED DESCRIPTION

Figure 1:
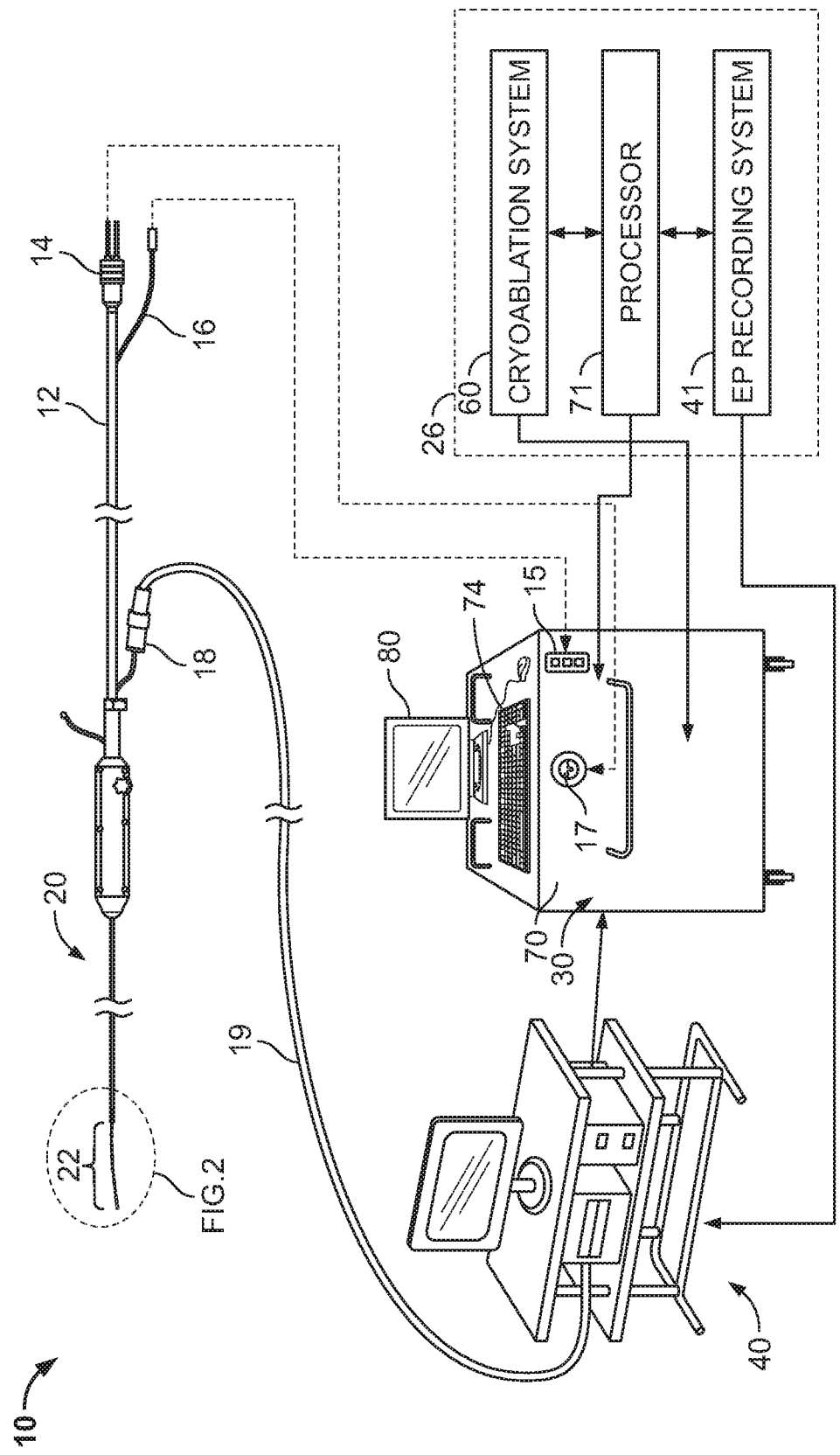
FIG. 1 is an illustration of a cryoablation system including a cryoablation catheter, according to an embodiment of the present invention.

The following disclosure provides for embodiments of tissue contact verification system with innovative features. These tissue contact verification systems are generally described in the context of cryoablation systems and cryoablation catheters. However, it should be understood that features of the disclosed systems can be applicable to other ablation technologies such as, for example, microwave, ultrasound, HIFU, RF, etc. In addition, the embodiments of the present invention disclosed herein have applicability outside the ablation technologies and can be used with any medical devices to determine/confirm contact between the medical device and tissue. Moreover, while several components, techniques and aspects have been described with a certain degree of particularity, it is manifest that many changes can be made in the specific designs, constructions and methodology herein above described without departing from the spirit and scope of this disclosure.

It is to be understood that the embodiments of the invention described herein are not limited to particular variations set forth herein as various changes or modifications may be made to the embodiments of the invention described and equivalents may be substituted without departing from the spirit and scope of the embodiments of the invention. As will be apparent to those of skill in the art upon reading this disclosure, each of the individual embodiments described and illustrated herein has discrete components and features that may be readily separated from or combined with the features of any of the other several embodiments without departing from the scope or spirit of the embodiments of the present invention. In addition, many modifications may be made to adapt a particular situation, material, composition of matter, process, process act(s) or step(s) to the objective(s), spirit or scope of the embodiments of the present invention. All such modifications are intended to be within the scope of the claims made herein.

Moreover, while methods may be depicted in the drawings or described in the specification in a particular order, such methods need not be performed in the particular order shown or in sequential order, and that all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It will be understood that when an element is referred to as being "connected" or "coupled" to another element, it can be directly connected or coupled to the other element or intervening elements may be present. In contrast, if an element is referred to as being "directly connected" or "directly coupled" to another element, there are no intervening elements present.

It will also be understood that, although the terms first, second, etc. may be used herein to describe various elements, these elements should not be limited by these terms. These terms are only used to distinguish one element from another. Thus, a first element could be termed a second element without departing from the teachings of the present invention.

Language of degree used herein, such as the terms "approximately," "about," "generally," and "substantially," represent a value, amount, or characteristic close to the stated value, amount, or characteristic that still performs a desired function or achieves a desired result. For example, the terms "approximately," "about," "generally," and "substantially" may refer to an amount that is within less than or equal to 10% of, within less than or equal to 5% of, within less than or equal to 1% of, within less than or equal to 0.1% of, and within less than or equal to 0.01% of the stated amount. If the stated amount is 0 (e.g., none, having no), the above recited ranges can be specific ranges, and not within a particular % of the value. Additionally, numeric ranges are inclusive of the numbers defining the range, and any individual value provided herein can serve as an endpoint for a range that includes other individual values provided herein. For example, a set of values such as 1, 2, 3, 8, 9, and 10 is also a disclosure of a range of numbers from 1-10, from 1-8, from 3-9, and so forth.

Some embodiments have been described in connection with the accompanying drawings. The figures are drawn to scale, but such scale should not be limiting, since dimensions and proportions other than what are shown are contemplated and are within the scope of the disclosed inventions. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

While a number of embodiments and variations thereof have been described in detail, other modifications and methods of using the same will be apparent to those of skill in the art. Accordingly, it should be understood that various applications, modifications, materials, and substitutions can be made of equivalents without departing from the unique and inventive disclosure herein or the scope of the claims.

System Overview

FIG. 1 illustrates a cryoablation system 10 according to an embodiment of the present invention, comprising a cryoablation console 30 and a cryoablation catheter 20 detachably connected to the console via a flexible cable 12. The flexible cable 12 terminates in a fluid connector 14 which is adapted to detachably attach with fluid-tight receptacle 17 on the console.

A temperature line 16 is also shown extending from cable 12. Temperature line 16 is detachably connectable to the console through the use of temperature ports 15.

In operation, as will be described in more detail herein, activation of the catheter causes a cryogen to be circulated through the distal treatment section 22 of the catheter. Tissue in contact with the distal treatment section 22 is cooled to a temperature sufficient to cause tissue necrosis. Temperature sensors or thermocouples present on the distal section (or elsewhere along the cryogen flow path) measure temperature. The temperature information is transmitted to the console 30 in real time, serving to measure and control cooling power during a surgical procedure. Examples and further details of cryoablation catheter systems are described in U.S. Pat. Nos. 7,410,484; 7,273,479; and 8,740,891; as well as International Patent Application No. PCT/US2014/056839, filed Sep. 22, 2014, entitled ENDOVASCULAR NEAR CRITICAL FLUID BASED CRYOABLATION CATHETER AND RELATED METHODS, the entire contents of each are incorporated herein by reference in their entirety for all purposes.

FIG. 1 also shows an electrophysiology (EP) recording system 40 adapted to record ECG signals. The EP recording system 40 is electrically coupled to cryoablation catheter 20 via connector 18 and flexible cable 19. Electrodes present on the distal treatment section 22 of cryoablation catheter 20, which shall be described in more detail herein, collect electrical information (e.g., cell voltage potentials for ECG readings, resistance, reactance, etc.) for determining catheter position, tissue contact, and/or treatment efficacy. The EP system may be a commercially available unit, such as, for example, the LabSystem PRO EP Recording System manufactured by Boston Scientific Inc. (Marlborough, Mass.). However, other EP systems may be used as described further herein.

The console 30 may house a variety of components (not shown) useful in operation of the cryoablation system including, without limitation, a controller, fluid tanks, valves, custom circuits, generators, regulators, pumps, etc. Examples of some of the components are described in U.S. Pat. Nos. 7,410,484; 7,273,479; and 8,740,891, the entire contents of each are incorporated herein by reference in their entirety for all purposes.

The console 30 includes a display 80 as shown in FIG. 1. In some embodiments, the display 80 is touch screen operable. The console 30 may also include other input devices such as, for example, a mouse and/or keyboard 74 to allow the user to input data and control the cryoablation system 10 and/or other devices.

The cryoablation system 10 preferably includes a processor 70, which is configured or programmed to control, for example, cryogen flowrate, pressure, and catheter temperatures as described herein. In some embodiments, as will be discussed further herein, the processor 70 can be programmed to receive electrical activity data (e.g. ECG recordings) from the EP recording system 40, and to determine tissue contact, catheter position, treatment efficacy, all of which may be indicated on display 80. It should also be understood that although the EP recording system 40 is shown physically separate from the cart 30, in other embodiments, the cart 30 includes or incorporates one or more of the components of the EP recording system (e.g. an amplifier, processor, circuits, etc.).

In embodiments of the present invention, the cryoablation system 10 includes a tissue contact verification system 26. In some embodiments, the tissue contact verification system 26 includes an EP recording module 41, a cryoablation system module 60, and a processor 71, all of which may be housed and interconnected within one convenient user-friendly console.

In other embodiments, the functional modules are physically separated but adapted to communicate with one another via wire or wireless transmission of data and information. And, as will be discussed further herein, the processor 71 can be programmed to automatically determine tissue contact and treatment efficacy based on data received from both the EP recording system or the EP recording module 41 and the cryoablation system module 60.

Catheter Detail

Figure 2:
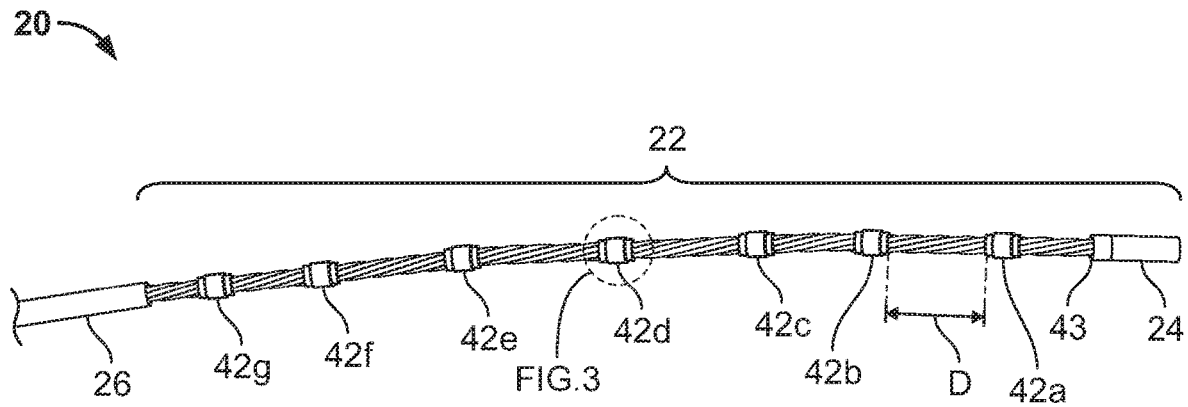
FIG. 2 is a partial perspective view of a cryoablation catheter including a plurality of electrodes, according to an embodiment of the present invention.

FIG. 2 shows an enlarged view of the distal treatment section 22 of the catheter 20 shown in FIG. 1. The distal section treatment section 22 contacts and freezes the target tissue. A plurality of electrodes 42 are disposed along the distal treatment section 22 for sensing and providing electrical information/signals at the treatment site during a treatment. In the embodiment depicted in FIG. 2, electrodes 42a-42g are included. As will be discussed in greater detail below, the tissue contact system measures/monitors electrical activity/signals between adjacent electrodes, i.e., between pairs of electrodes, for example, between electrode 42a and electrode 42b, between electrode 42b and electrode 42c, etc. Using pairs of electrodes permits bipolar recording of the electrical activity/signals in the tissue at the treatment site.

As depicted in FIG. 2, the electrodes 42 are disposed in a lengthwise-spaced arrangement. Each electrode 42 is joined to a conducting wire that extends proximally to electrical connector 18. Notably, the electrodes 42 are shown situated within the energy delivery section (the distal treatment section 22), and are not included outside of the energy delivery section. As discussed further herein, placing the electrodes 42 within the treatment or energy delivery section provides more accurate electrical information in the treatment or energy delivery section 22 and therefore, a more accurate indication of the tissue contact than placing the electrodes outside of the treatment or energy delivery section 22, away from the tissue to be evaluated. In the embodiment shown in FIG. 2, the electrodes 42 are mounted on the freeze surface itself and measure/monitor the exact tissue location(s) within the freeze zone.

The spacing between the electrodes 42 may vary. In FIG. 2, for example, each electrode 42 is spaced a distance (D) from an adjacent electrode 42. The spacing distance (D) between the electrodes ranges from 0.5 to 25 mm. This spacing (D) can be uniform or it can vary between adjacent electrodes 42.

Additionally, the number of electrodes 42 may vary. In some embodiments, the number of electrodes 42 ranges from 2-20, more preferably ranges from 5-15, and in some embodiments, ranges from 8-12. The more electrodes 42 disposed along the distal treatment section 22, as will be discussed further herein, the more information that can be obtained from the treatment region for processing and analysis of catheter tissue contact and treatment efficacy.

The catheter 20 shown in FIG. 2 also includes a temperature sensor 43 (e.g., a thermocouple). Temperature sensor 43 is connected with the console 30 via temperature line 16 and temperature values may be utilized to adjust cooling power or energy during a treatment. Temperature sensors may also be disposed in line with the outflow and inflow of cryogen to measure a temperature difference between the inflow cryogen and outflow cryogen. The temperature difference may also be used to adjust cooling power to the tissue.

Figure 3:
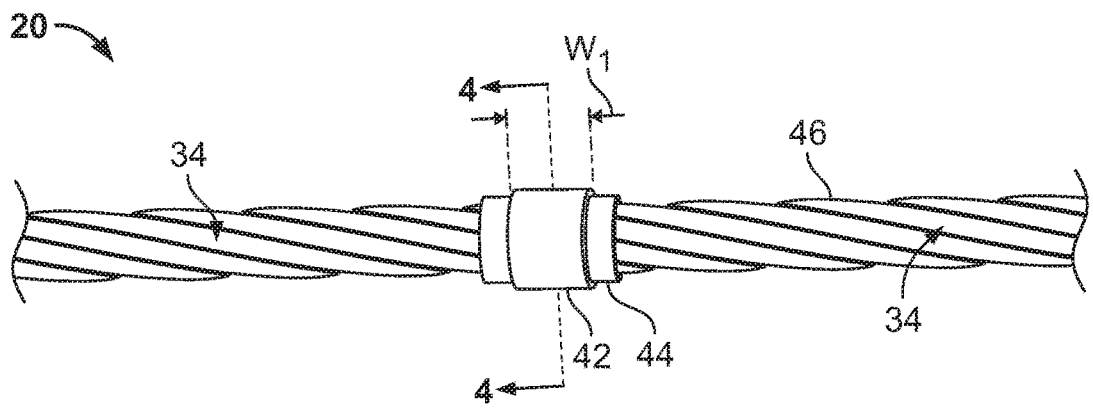
FIG. 3 is an enlarged view of a portion of the catheter shown in FIG. 2.
Figure 4:
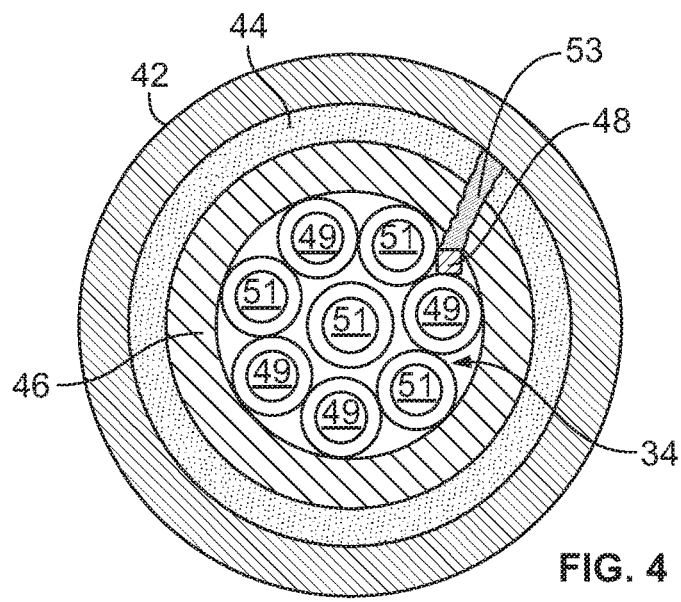
FIG. 4 is a cross sectional view of the catheter taken along line 4-4 in FIG. 3.

With reference to FIG. 3, an enlarged view of a portion of the distal treatment section 22 depicted in FIG. 2 is shown. A thin, thermally conducting sleeve 46 (e.g., PET sleeve) is shown coaxially surrounding the bundle 34 of cryogen fluid transport tubes. An electrode 42 in the form of a ring is attached to the sleeve 46 via an epoxy layer 44. The electrodes 42 may be made of platinum or another electrically conducting material. Although the electrode 42 embodiment in FIGS. 2-4 is in the shape of a ring, other shapes for the electrodes 42 may be used. The width ($W_1$) of an electrode 42 may range from about 0.5 to 10 mm, and in embodiments, is preferably about 1 mm.

FIG. 4 shows a cross sectional view of the distal treatment section 22 of catheter 20 taken along line 4-4 in FIG. 3. A bundle 34 of cryogen fluid transport tubes form a circular array. The tube array 34 includes a plurality of inlet/delivery fluid transfer tubes 49 and a plurality of outlet/return fluid transfer tubes 51. In the embodiment shown in FIGS. 3-4, the plurality of inlet fluid transfer tubes 49 and a plurality of outlet fluid transfer tubes 51 are arranged in a twisted bundle. However, the tubes in the bundle 34 may be arranged in a variety of other configurations including, for example, positioning the inlet fluid transfer tubes 49 along the exterior of the bundle 34 and positioning the outlet fluid transfer tubes 51 on the interior of the bundle 34.

The inlet/delivery fluid transfer tubes 49 and outlet/return fluid transfer tubes 51 may be made of various materials. In some embodiments, the tubes are made of polyimide.

The size of the fluid transport tubes 49, 51 may vary. In some embodiments, the fluid transport tubes 49, 51 have an inner diameter in the range of approximately 0.02 to 0.1 inches. In some embodiments, the tubes have a wall thickness of approximately 0.002 inches.

During operation, the cryogen fluid is delivered to the catheter through a supply line from a suitable nitrogen source at a temperature of approximately −200° C. The cryogen is circulated through the multi-tubular 34 freezing zone provided by the exposed fluid transfer tubes 49, 51. The catheter may terminate at an endcap (e.g., endcap 24 as shown in FIG. 2). Endcap 24 may include an internal channel or chamber to fluidly connect the inlet fluid transfer tubes 49 to the outlet fluid transfer tubes 51.

In some embodiments, the cryogenic fluid utilized is nitrogen. In some embodiments, the nitrogen is supplied and maintained near it critical point (critical temperature of −147° C. and critical pressure of 492 psi). However, other cryogenic fluids may be utilized such as argon, neon, helium and others. In embodiments, the cryogen may be provided directly by the medical facility via a pressurized supply line. The system can include regulators and other devices to reduce or increase the pressure to the near critical pressure and temperature as desired. Other cryogenic fluid supply sources include, without limitation, a tank under pressure, mechanical pump, and a cryogen generator. Examples of such cryogenic fluid supply/generating sources are disclosed in U.S. Pat. No. 7,410,484, entitled "CRYOTHERAPY PROBE", filed Jan. 14, 2004 by Peter J. Littrup et al.; U.S. Pat. No. 7,083,612, entitled "CRYOTHERAPY SYSTEM", filed Jan. 14, 2004 by Peter J. Littrup et al.; U.S. Pat. No. 7,273,479, entitled "METHODS AND SYSTEMS FOR CRYOGENIC COOLING" filed Sep. 27, 2004 by Peter J. Littrup et al. U.S. Pat. Nos. 7,410,484, 7,083,612 and 7,273,479, the entire contents of each are incorporated herein by reference in their entirety for all purposes.

In embodiments, the nitrogen flow does not form gaseous bubbles inside the small diameter inlet fluid transfer tubes 49 and outlet fluid transfer tubes 51 under any heat load, so as to not create a phenomenon known as vapor lock, which limits/blocks the flow of nitrogen, which adversely affects the cooling power of the system. By operating the system at the near critical condition of nitrogen for at least an initial period of energy application, vapor lock is eliminated as the distinction between the liquid and gaseous phases disappears.

FIG. 4 also shows a conductive wire/element 48 in electrical connection with the electrode 42. Conductive wire/element 48 extends proximally to send electrical data/signals from the electrode 42 to the processor. The wire 48 may be soldered 53 or otherwise connected to the electrode 42 using other methods known to those of skill in the art (e.g., by use of electrically conducting adhesives, etc.).

In embodiments, and although not shown, the distal treatment section 22 of the catheter 20 may be deflectable. For example, either the fluid transport tubes themselves, or an ancillary element (e.g., and without limitation, a spine, stylet or shell member) can be used and can be, for example, made of a shape memory material such a nitinol, deflectable, or steerable to allow a user to manipulate the distal treatment section to make continuous and firm contact between the energy delivery elements and the target tissue. In some embodiments, the catheter configurations include substantial bends, or loops (e.g., full 360 degree loop-shape) which provide both the circumferential, as well as linear, ablations to mimic the surgical Maze procedure noted above. The catheters described herein may be manipulated (e.g., controllably deflected) to form ring-shaped lesions near or around the pulmonary vessel entries. Further examples of deflectable cryoablation catheters are described in PCT/US2015/024778, filed Apr. 7, 2015, entitled Endovascular Near Critical Fluid Based Cryoablation Catheter Having Plurality of Preformed Treatment Shapes, the entire contents of which are incorporated herein by reference in their entirety for all purposes.

Applications

The systems and methods described herein may be used in a variety of medical applications including, for example, cardiovascular applications. Examples of cardiovascular applications include, without limitation, treatment of arrhythmias such as atrial fibrillation and atrial flutter.

Figure 5:
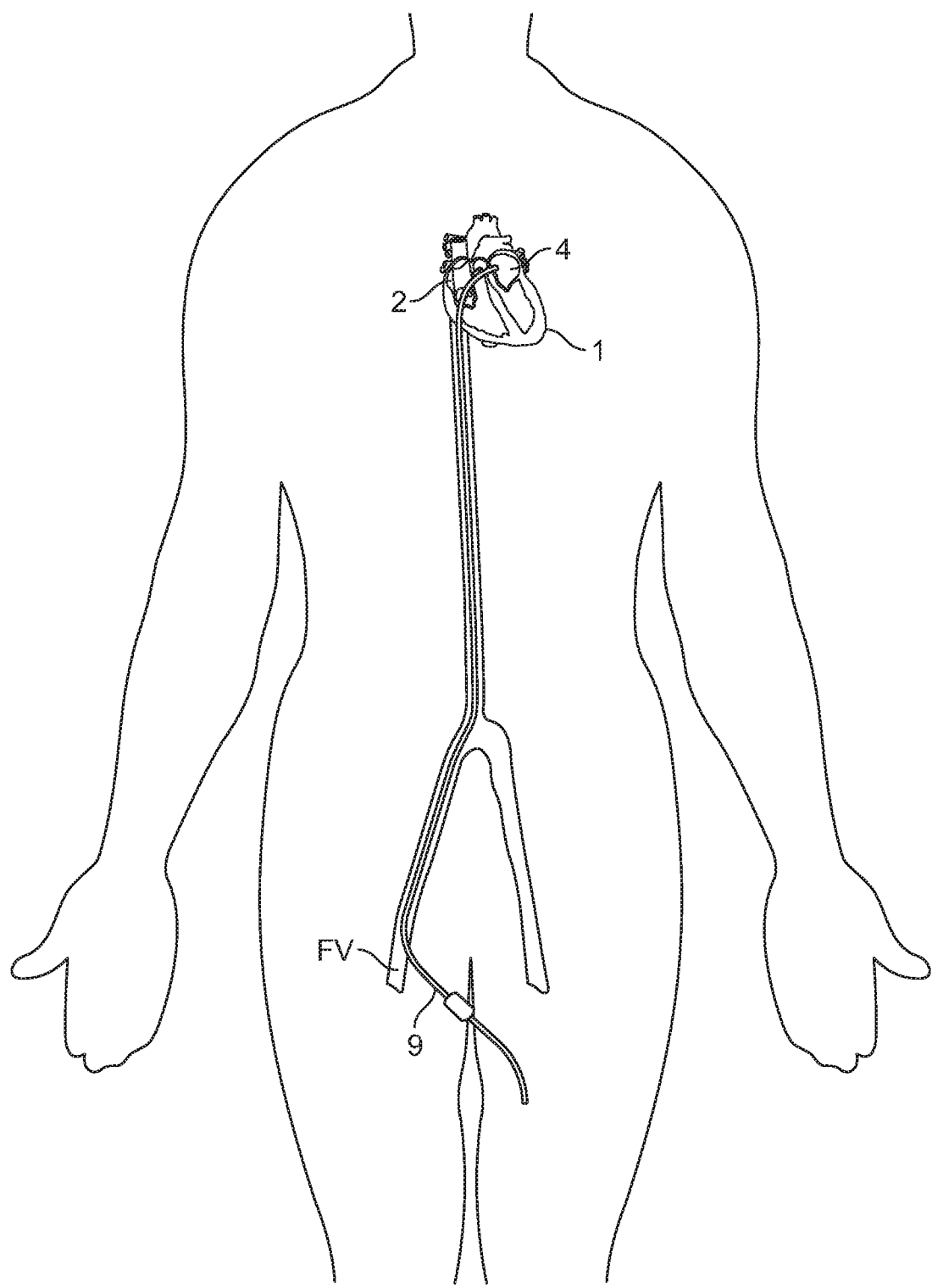
FIG. 5 is an illustration of an endovascular catheterization to access the heart, according to an embodiment of the present invention.
Figure 6:
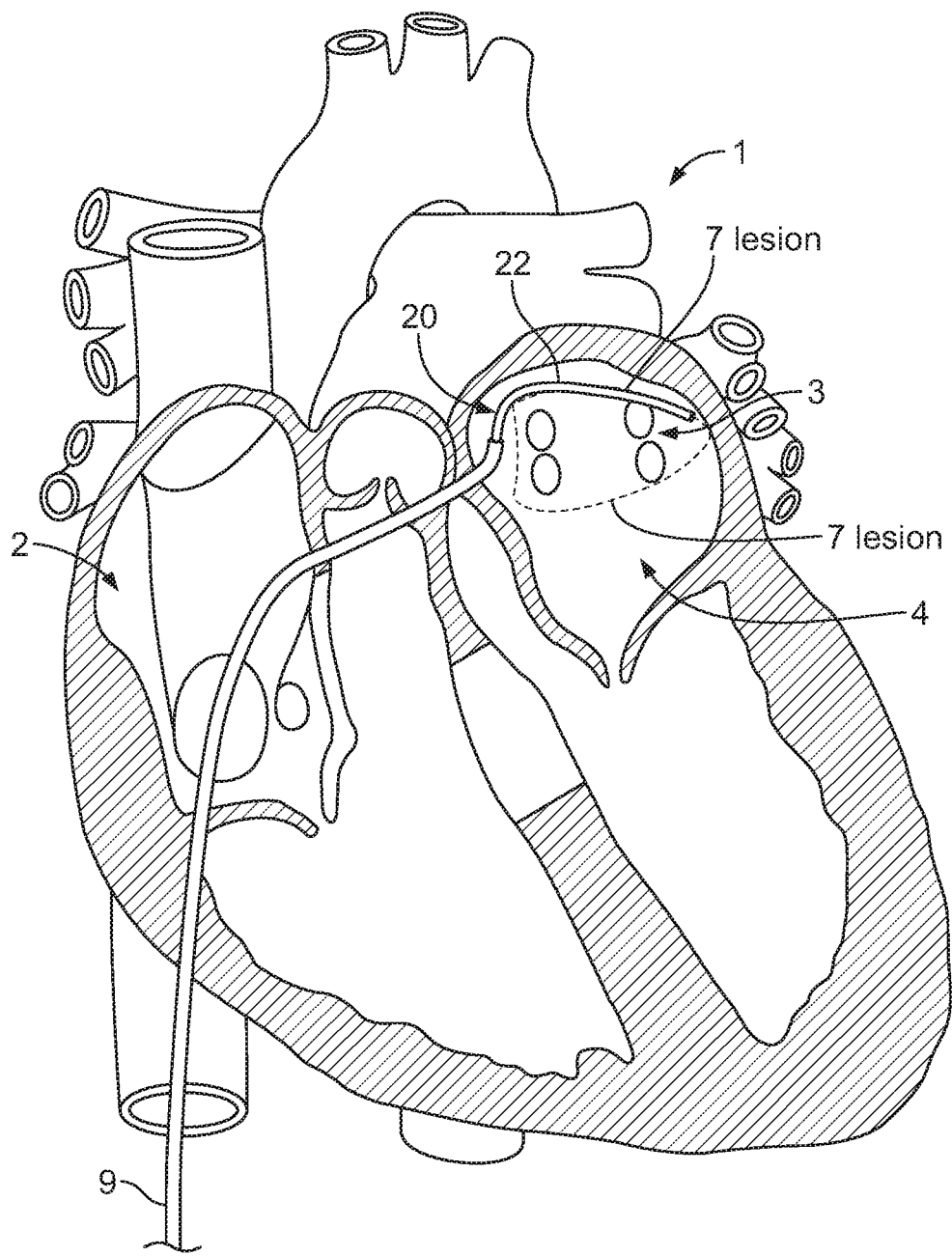
FIG. 6 is an illustration of a distal section of a cryoablation catheter placed in a chamber of the heart, according to an embodiment of the present invention.

With reference to FIGS. 5-6, a cardiovascular application for treating atrial fibrillation is shown. In particular, FIGS. 5-6 illustrate creating an elongate, continuous lesion along the inner wall of the heart 1 in the left atrium 4. Creating such a lesion is known to be effective for treating various conditions such as, for example, atrial fibrillation because such continuous lesions electrically isolate the pulmonary veins 3. Further details of cryoablation systems and methodology are described in, for example, International Patent Application No. PCT/US2015/024778, filed Apr. 7, 2015, entitled Endovascular Near Critical Fluid Based Cryoablation Catheter Having Plurality of Preformed Treatment Shapes, the entire contents of which are incorporated herein by reference in their entirety for all purposes.

The example shown in FIGS. 5-6 and following discussion tends to focus on embodiments for performing the left atrium lesion of the Cox maze VII procedure, however, the procedure for producing these lesions can be used to create other lesions in an around the heart and other organs. Additional lesions of the Cox maze VII procedure, as well as other variations of the Cox Maze treatments may be carried out using steps and devices described herein. Additional techniques and devices are described in international patent application nos. PCT/US2012/047484 to Cox et al. and PCT/US2012/047487 to Cox et al. corresponding to International Publication Nos. WO 2013/013098 and WO 2013/013099 respectively, the entire contents of each are incorporated herein by reference in their entirety for all purposes.

With reference to FIG. 5, one technique to reach the left atrium with the distal treatment section 22 of a catheter 20 is illustrated. A peripheral vein (such as the femoral vein FV) is punctured with a needle. The puncture wound is dilated with a dilator to a size sufficient to accommodate an introducer sheath, and an introducer sheath with at least one hemostatic valve is seated within the dilated puncture wound while maintaining relative hemostasis. With the introducer sheath in place, the guiding catheter or sheath 9 is introduced through the hemostatic valve of the introducer sheath and is advanced along the peripheral vein, into the target heart region (e.g., the vena cavae, and into the right atrium 2). Fluoroscopic imaging can be used to guide the catheter to the selected site.

Once in the right atrium 2, the distal tip of the guiding catheter 9 is positioned against the fossa ovalis in the intraatrial septal wall. A needle or trocar is then advanced distally through the guide catheter until it punctures the fossa ovalis. A separate dilator may also be advanced with the needle through the fossa ovalis to prepare an access port through the septum for seating the guiding catheter. The guiding catheter or sheath 9 thereafter replaces the needle across the septum and is seated in the left atrium through the fossa ovalis, thereby providing access for other devices through its own inner lumen and into the left atrium.

Other left atrial access methods may be suitable substitutes for using the ablation device assembly of the present invention. In one alternative, a "retrograde" approach may be used, wherein the guiding catheter is advanced into the left atrium from the arterial system. In this variation, the Seldinger technique may be employed to gain vascular access into the arterial system, rather than the venous, for example, at a femoral artery. The guiding catheter is advanced retrogradedly through the aorta, around the aortic arch, into the ventricle, and then into the left atrium through the mitral valve.

FIG. 6 shows an endocardial catheter 20 advanced through the guide catheter 9 and deployed as described herein to establish the desired lesion in the left atrium 4. The distal treatment section 22 of the endocardial catheter 20 is deflected within the endocardial space, preferably contacting the endocardial wall of the left atrium. This is illustrated in FIG. 6, where the distal treatment section 22 has been configured and deflected to cover the superior left atrial lesion 7, which partially encircles the left pulmonary veins 3. Although in the embodiment depicted in FIG. 6, the distal treatment section 22 is shown as only partially encircling the left pulmonary veins 3, in other embodiments, the distal treatment section 22 can be designed and configured to be manipulated to completely encircle the left pulmonary veins 3, thereby forming a single, continuous lesion that completely encircles the pulmonary veins.

Tissue Contact Verification

Described herein are systems, apparatuses and methods for verifying contact between the distal treatment section (e.g., distal treatment section 22 shown in FIGS. 1-2) of a catheter and the target tissue to be treated (e.g., the tissue area corresponding to lesion 7 shown in FIG. 6).

Figure 7:
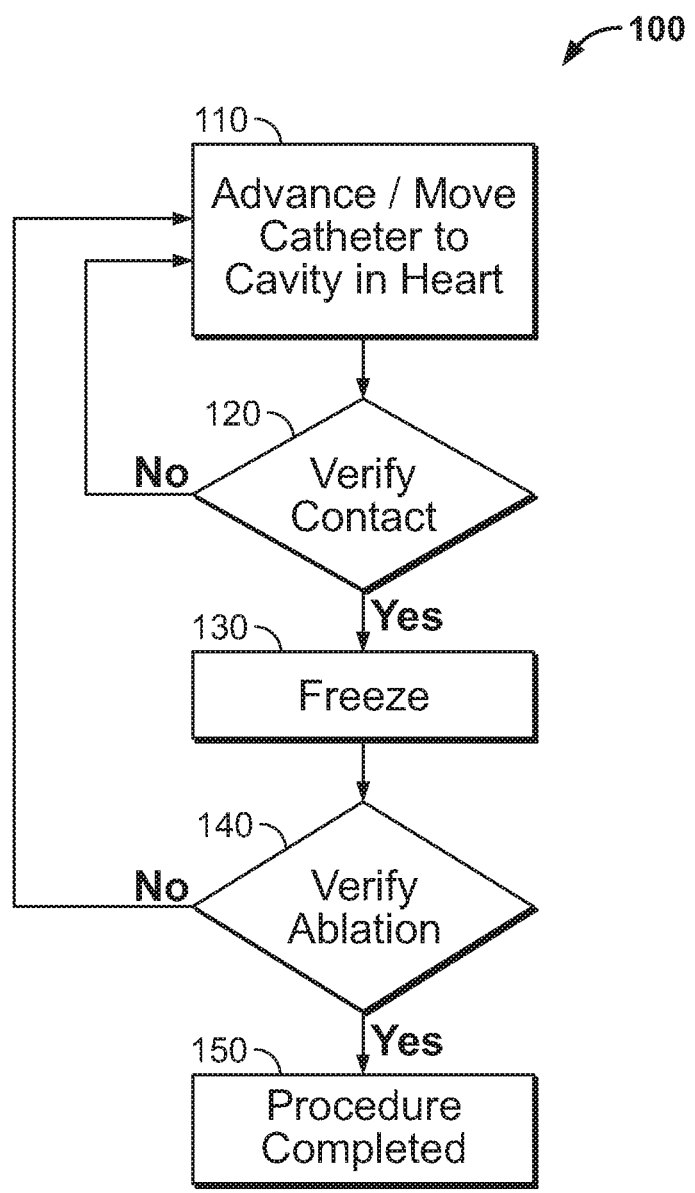
FIG. 7 is a flowchart showing a method for evaluating efficacy of a treatment procedure, according to an embodiment of the present invention.

With reference to FIG. 7, a flowchart illustrates the steps of a method 100 according to an embodiment of the present invention, for verifying tissue contact between a catheter or other ablation device, for example, a cryoablation catheter as disclosed and described herein, and the target tissue. In this embodiment, the disclosed method is used for verifying/confirming contact between a cryoablation catheter and cardiac tissue.

Initially, and indicated by reference numeral 110, a cryoablation catheter as described herein is advanced into the applicable cavity of the organ (or chamber of the heart). For example, the distal treatment section 22 of catheter 20 may be advanced into the right atrium and positioned such that the most distal electrode is in contact with the ventricular end of the cavo tricuspid isthmus (CTI) (A:V electrogram amplitude ratio of ~1:2) for the treatment of atrial flutter.

Step 120 recites to verify/confirm tissue contact by the distal treatment section 22. This step is carried out by sensing electrical activity through the electrodes 42 present on the distal treatment section 22 as discussed further herein in connection with FIG. 8, below. If the electrical information/signals received from the electrodes 42 indicate that suitable tissue contact has not been achieved, the catheter 20 is then moved to a new position in closer proximity to the target tissue or manipulated in its current position in an attempt to achieve better contact with the target tissue. Fluoroscopy may be used to assist the surgeon in determining positional information. Step 120 is repeated until tissue contact is confirmed by the electrical signals received from the electrodes 42.

Step 130 is ablating or freezing the target tissue to create the lesion. The distal treatment section of the catheter is activated by circulating the cryogen through the distal treatment section. Tissue in contact with the distal treatment section is then ablated/frozen, causing necrosis.

Step 140 is to verify or confirm tissue necrosis following ablation. As discussed further herein in connection with FIG. 8, in embodiments, pretreatment data is compared with post treatment data.

If the ablation treatment is sufficient or within a threshold range, the treatment procedure may be deemed completed as indicated by step 150. If, on the other hand, the degree of ablation (or tissue necrosis) is not sufficient, the surgeon may return to step 110, and repeat the process as desired.

Example 1

Figure 8:
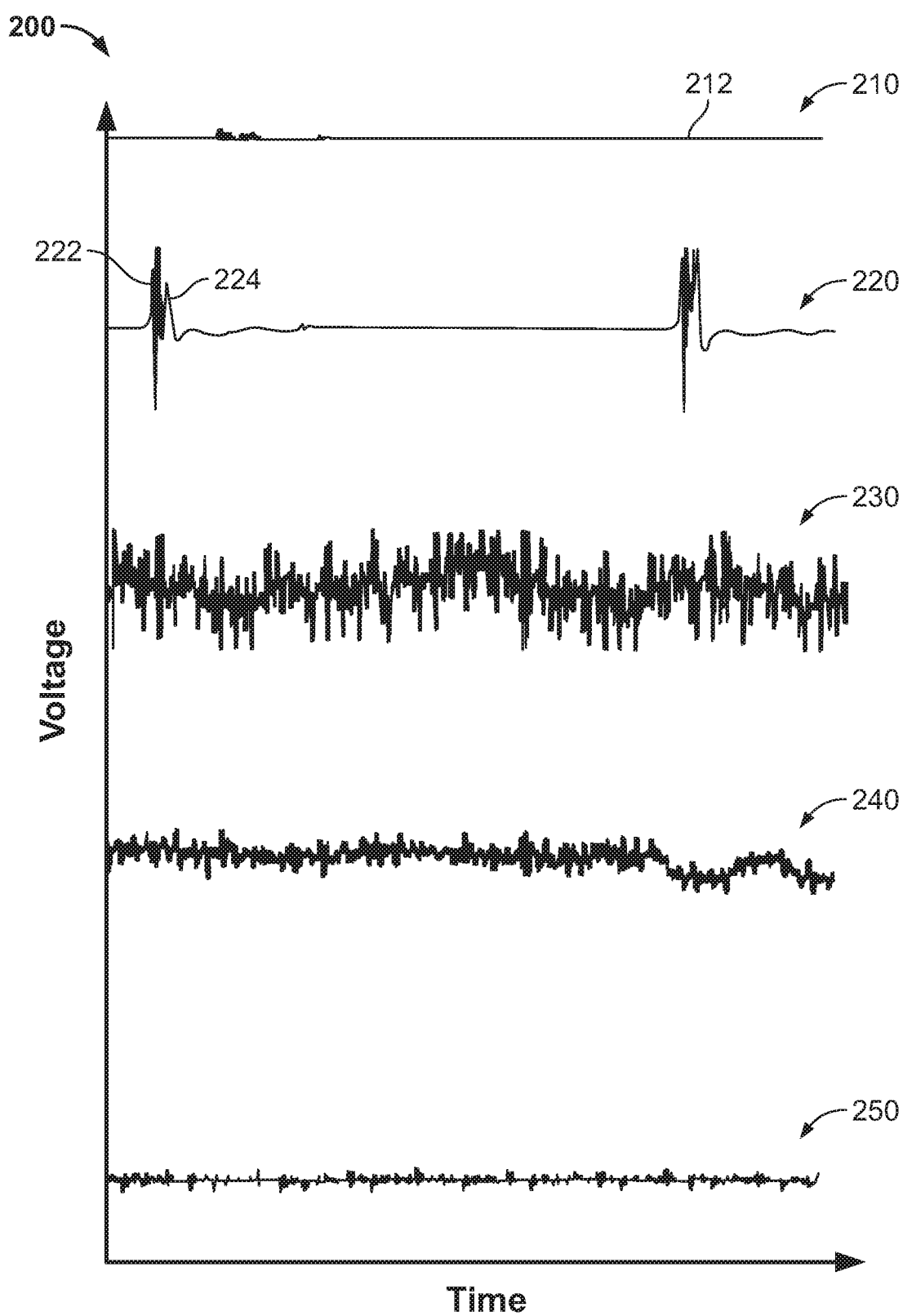
FIG. 8 is a graph illustrating electrical activity between an electrode pair during various treatment stages of a cryoablation procedure, according to an embodiment of the present invention.

FIG. 8 is a graph 200 of ECG recordings (or signatures/signals) indicative of the electrical activity during a cryoablation procedure performed on healthy porcine tissue. The signatures were obtained by measuring electrical activity between a first electrode and a second electrode axially spaced from the first electrode (an electrode pair as discussed in more detail below).

Experiment Setup. A cryoablation system as described above in connection with FIGS. 1-4 was provided. The electrodes were connected to an ECG recorder system (GE Healthcare CardioLab II EP Recording System, Manufactured by GE Healthcare, USA.)

Initially, and with reference to signature 210, the distal section of the catheter was endovascularly advanced into the Right Atrium, near the Cavo Tricuspid Isthmus (CTI) of the heart, and spaced from the heart walls. The distal section of the catheter was surrounded by blood. The electrical activity recorded on the ECG system shows a relatively flat line 212, indicating that there was essentially no electrical activity measured arising from the beating heart. This flat curve 212 is anticipated because the blood does not conduct electrical current well from one electrode to the next electrode. This step may be used as a control signature/signal or baseline and compared to the ECG signatures/signals corresponding to the other stages of the treatment procedure.

Next, the distal treatment section (e.g. section 22 of FIGS. 1 and 2), is advanced or otherwise manipulated into contact with the target tissue (here, the atrium wall). A clear signature/signal 220 arises from the tissue contact as measured by the electrode pair and ECG system. Depolarization of the cells (or voltage vs. time) is measured by the electrode pair in direct contact with the tissue. The signature/signal is characterized by regular peaks 222, 224 indicative of the heart beat. This implies the catheter distal treatment section portion between the first electrode to the second electrode (for example, electrodes 42a and 42b in FIG. 2), is in direct contact with the cardiac tissue. Tissue contact adjacent these two electrodes is thus verified/confirmed because a clear cardiac signature/signal 220 is measured by the electrode pair.

In some embodiments, the distal treatment section 22 includes additional electrode pairs for analyzing tissue contact of additional portions of the catheter treatment section. Should no electrical activity be indicated after attempting to place the catheter against the target tissue, the catheter is further adjusted, deflected or moved. And an ECG signature may be analyzed for tissue contact. Thus, referring to FIG. 2, the graph of the ECG recordings depicted in FIG. 8, may be for electrodes 42a and 42b. Additional electrode pairs such as, for example, electrodes 42b and 42c may be connected to the ECG recording system to generate a graph similar to the graph in FIG. 8, of ECG signatures/signals for this pair of electrodes. In other embodiments, all of the electrode pairs (i.e., electrodes 42a and 42b, electrodes 42b and 42c, electrodes 42c and 42d, electrodes 42d and 42e, electrodes 42e and 42f, and electrodes 42f and 42g) may be connected to the ECG recording system to generate graphs of ECG signatures/signals for all of the electrode pairs on the distal treatment section. Connecting all of the electrode pairs to the ECG recording system permits a physician to obtain a complete picture of the entire distal treatment section contact with the target tissue.

Next, and without relocating or otherwise moving the catheter's distal treatment section, the cryoablation system and hence, the catheter was activated. In this embodiment, a near critical cryogen was circulated through the tube bundle in the distal treatment section of the catheter. The tissue in contact with the distal treatment section was ablated/frozen, forming a lesion Simultaneously, electrical activity between the first and second electrodes was recorded. This electrical activity is shown as signature 230 in FIG. 8. The signature 230 reflects the catheter as being activated because of the presence of the relatively high amplitude, and numerous scattered peaks, which are indicative of high noise.

Signature 240 reflects the electrical activity after halting the ablation. Although there is still some noise, the amplitude and number of peaks are minimized. Without being bound by theory, it is thought that the formation of ice in the tissue or surrounding the electrodes causes some electrical activity, and as the ice continues to melt or warm, the electrical activity and hence, the noise, is reduced.

The electrical information/signals received during these "Freeze On" and "Freeze Off" states is not only informative as to the conditions at the treatment site/target tissue, the information also increases safety. In particular, a physician can confidently know when to withdraw or move the cryoablation catheter from the target tissue subsequent to freezing the tissue. In stark contrast, failure to wait for the proper time to move the catheter away from the frozen tissue can cause collateral damage to the tissue because the catheter distal treatment section may still be stuck to the tissue during movement. With reference to signature 240 again, an electrical activity measured in the target tissue is shown to be minimal, or below a threshold value and thus, the surgeon may safely move the ablation catheter.

Next, and while the distal treatment section remains in the identical position as the preceding steps, the electrical activity is again measured/monitored. With reference to signature 250, little or no voltage is measured in comparison to peaks 222, 224 of signature 220. This is because tissue necrosis has occurred in the target area as a result of the cryoablation and necrosed tissue is a poor electrical conductor.

The above steps serve to confirm tissue ablation or tissue necrosis at the target site. A pre-treatment signature such as, for example, signature 220 is observed and compared to a post-treatment signature such as, for example, signature 250. Notably, the treatment section of the cryoablation catheter (and the monitoring electrodes thereon) remain in place until the physician confirms the entire target area has been ablated. This fixed-position technique is advantageous because the sensed electrical activity corresponds exactly to the entire length of the ablated tissue area, and the electrical activity is monitored immediately following ablation. Tissue necrosis and the absence of electrical activity along the entire length of target tissue can be confirmed, reflecting an effective ablation treatment.

Arrhythmia Treatment Efficacy

Additionally, in some embodiments, a method further includes determining treatment efficacy for various arrhythmias including, for example, atrial fibrillation and atrial flutter. Whether the physician performs a Pulmonary Vein Isolation (PVI) approach with entrance and exit blocks for the treatment of atrial fibrillation or a bidirectional block approach for the treatment of atrial flutter, potentials are monitored across the ablation area to confirm successful blocking of abnormal electrical signals.

In embodiments, the cryoablation catheter (e.g., catheter 20 discussed above) is used as a diagnostic catheter (e.g., a circular mapping catheter) in addition to being used as an ablation catheter. For example, immediately following ablation in a PVI, the cryoablation catheter is advanced more distally inside a specific pulmonary vein to measure pulmonary vein potentials (voltage). Because the cryoablation catheter acts both as an ablation catheter and a diagnostic mapping catheter, there is no need for additional diagnostic mapping catheters (e.g., a lasso-type mapping catheter).

In other embodiments for determining treatment efficacy, intracardiac diagnostic catheters are provided in addition to the cryoablation catheter. For example, pacing catheters may be positioned at the coronary sinus artery and pace toward the left pulmonary veins, and/or the superior vena cava (SVC) and paced toward the right pulmonary veins. Additional diagnostic mapping catheters may be placed in the heart at, for example, the right atrium and the right ventricle. Examples of diagnostic catheters include but are not limited to: the deflectable Halo catheter (Cordis Webster, Baldwin Park, Calif.), the decapolar catheter (Daig, Minnetonka, Minn.), and the quadrapolar catheter (Cordis Webster, Baldwin Park, Calif.). Details of intracardiac mapping following a PVI ablation are disclosed in, for example, Journal of Atrial Fibrillation, October-November, 2013, Vol. 6, Issue-3, Electrophysiological Evaluation of Pulmonary Vein Isolation, by S. Kircher, P. Sommer.

Additionally, in embodiments, standard patch electrode ECG recordings (e.g., 12 lead waveforms and Holter monitoring) are evaluated before and after treatment to determine whether the disease or condition is alleviated. Follow up studies and monitoring may be performed at, for example, 2, 6, and 12 months following the surgery.

The tissue verification system described herein may have various embodiments. As shown in FIG. 1, for example, the tissue contact verification system may include a cryoablation catheter, a cryoablation console for driving and controlling the cooling power of the cryoablation catheter, and an ECG recording system which is physically separate from the cryoablation power console. A commercially available EP recorder may be provided which includes a standard receptacle for mating with the connector from the cryoablation catheter, and for receiving the electrical data during a procedure as described above. The EP recorder system may be operated to display the electrical ECG system arising from the cryoablation catheter electrodes. Depending on the GUI and features of the particular EP system, the data may be displayed, and further processed variously. The signatures may be recorded, displayed and compared. Examples of EP recording systems include without limitation the LabSystem PRO EP Recording System manufactured by Boston Scientific Inc. (Marlborough, Mass.). However, other EP systems may be used.

In another embodiment, the cryoablation system includes a computer programmed to receive electrical information (signals) from the EP recording system and to compute the tissue contact, freeze state, and treatment efficacy information. The cryoablation console may include an adapter or electrical receptacle to electrically communicate with the EP recording system. The computation step is automatic, and not subject to operating the EP recorder on a procedure by procedure basis to analyze data from the cryoablation catheter electrodes.

In another configuration, the EP recording system and the cryoablation system are provided as a standalone system (e.g., single console or cart). The system shares components such as, for example, a programmed processor for receiving the electrical activity from the electrodes on the distal treatment section. The processor may be programmed to process the electrical signals including without limitation, removing noise, identifying peaks and valleys, computing values of resistance, impedance, and capacitance, and comparing individual signatures with one another (such as baseline signatures to ablation signatures and baseline signatures to post-ablation signatures, etc.). Output may be displayed on a monitor in communication with the processor. Indicia may show levels of tissue contact, or length of the distal treatment section in contact with the target tissue based on which electrode pairs signals are indicating contact.

In embodiments, the cryoablation processor is programmed to not activate ("FREEZE-ON") until tissue contact is verified. This step would avoid activating the catheter inconsistently or when there is incomplete contact with the tissue.

In some embodiments, the processor may be programmed to display a model catheter, the target tissue, color indicia representative of tissue contact, beacons, and symbols. In embodiments, the output is of a quantitative sort and based on tissue contact data, target tissue data, and design parameters of the cryoablation catheter in use (e.g., dimensions of the treatment section, bend angle, materials). Automatic computation and programming has advantages because the output can be less susceptible to interpretation, estimation and error. Thus, the processor can be programmed to interpret the electrical signatures/signals received from the electrode pairs and based on the type of signal received (for example, signatures 210, 220, 230 and 240) indicate to the user the quality and extent of contact, whether the catheter is freezing, whether ice exists in the target tissue, etc. Based on the processor's interpretation, this information can be presented to the doctor graphically, pictorially, using text, etc. For example, the distal treatment section of the catheter, including the electrodes, can be recreated on the display and then based on the processor's interpretation of the received electrical signals, the portions of the distal treatment section that are confirmed in contact with the target tissue can be highlighted. For example, portions of the distal treatment section that are in good contact with the target tissue can be green while portions of the distal treatment section that are not in contact with the target tissue can be red. Such a pictorial representation makes it easy for a doctor to quickly determine the contact conditions of the distal treatment section at the treatment location.

Electrical Resistance

FIG. 9A illustrates a distal treatment section of a cryoablation catheter 310 according to another embodiment of the present invention. The catheter 310 comprises 4 electrode sets (e.g., set 320).

With reference to FIG. 9B, each electrode set 320 has 2 electrodes 322, 324. The electrodes are shown as ring-shaped, and are mounted on a polymeric sleeve 323, which is adhered with epoxy 329 to the catheter shaft. The width ($W_2$) of each electrode may vary and in embodiments ranges from approximately 0.5 to 2 mm, and in one embodiment is approximately 1.0 mm.

The gap between the individual electrodes can vary. In some embodiments the gap (G) is approximately 1.0 mm. Additionally, the electrode sets 320 are spaced apart from one another. In some embodiments, the spacing ($D_2$) between the sets 320 is approximately 0.5 to 2.0 inches and in particular embodiments, the spacing ($D_2$) between the electrode sets 320 is approximately 1.0 inch.

The catheter shaft 331 may be made as described above and include, for example, a bundle of fluid transport tubes that comprise inlet fluid transfer tubes and outlet fluid transfer tubes to provide cooling power to the target tissue. Shape memory and/or spine elements may be incorporated into the device to control deflection, angle and size of the deployment shape including a loop as shown in FIG. 9A.

With reference to FIG. 9C, one or more conducting wires 326 extend proximally from the electrodes to a connector in the handle (not shown), which can be interfaced to the EP recording system to transmit electrical activity between the electrodes and a computer processor.

In embodiments depicted in FOGS. 9A-9C, each electrode set 320 is a bipolar pair (i.e., each electrode set 320 includes a first electrode 322 and a second electrode 324). Using 2 electrodes in this bipolar configuration is advantageous as it permits elimination or reduction of the common noise between the two electrodes. This also reduces the Seebeck effect. Thus, using this bipolar electrode configuration results in an improved signal to noise ratio and hence, a cleaner electrical or ECG signal.

Although the embodiment of the invention depicted in FIG. 9A includes four (4) electrode sets 320, any number of electrode sets 320, may be used.

Figure 10:
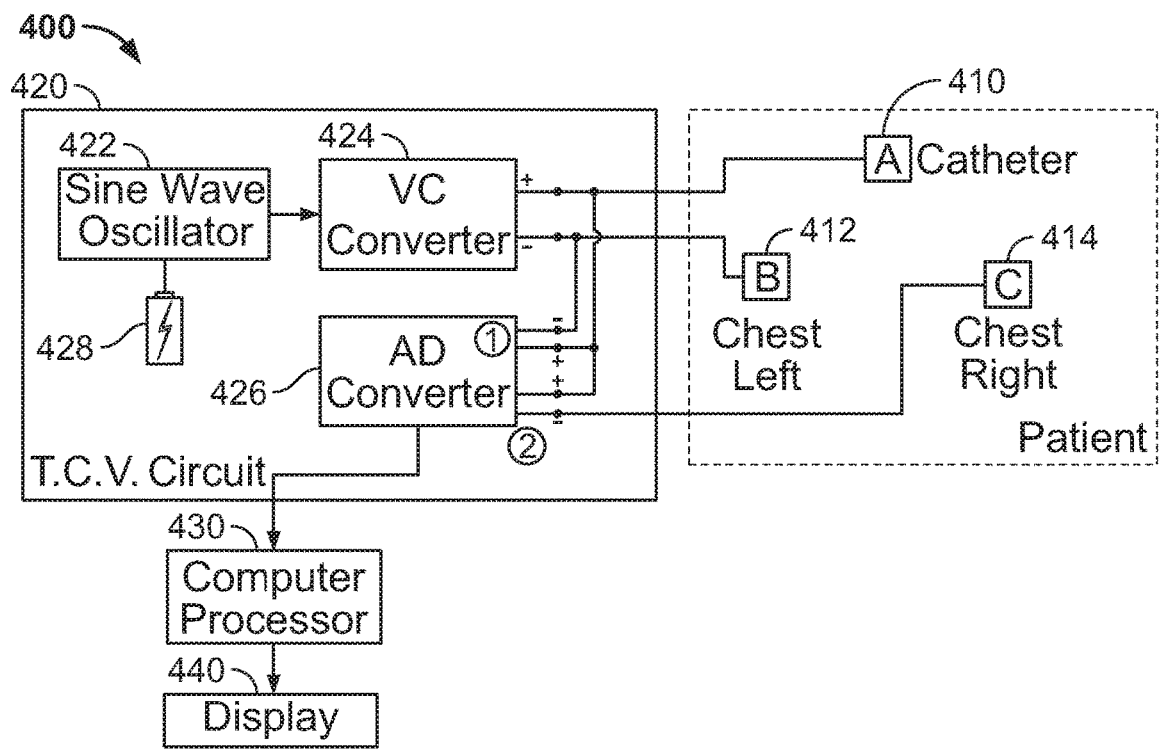
FIG. 10 is a schematic diagram of a system for verifying tissue contact, according to an embodiment of the present invention.

FIG. 10 is a schematic diagram of an embodiment a tissue contact verification system 400 incorporating a catheter 410 as shown in FIG. 9. The electrode sets 320 of the catheter 410 are connected to tissue contact verification (TCV) circuit 420. The TCV circuit 420 is shown having sine wave oscillator 422, and a voltage to current converter 424 for delivering current to the catheter electrode sets 320. A power source such as battery pack 428 may be included to deliver the initial DC current to wave oscillator 422. In embodiments, current from the current converter 424 is also sent to chest patch electrodes 412, 414 for recording baseline electrical activity and noise.

FIG. 10 also shows an analog to digital (AD) converter 426. The AD converter 426 receives electrical activity from the catheter, and left and right chest patch electrodes 412, 414 corresponding to Line (1) and Line (2) in FIG. 10.

As discussed further below, the digital information is sent to computer 430 for processing. Indicia of tissue contact between the catheter and tissue may be presented on display 440. An example of a circuit for measurement of electrical activity is described in U.S. Pat. No. 8,449,535 to Deno et al.

Example 2

Figure 11:
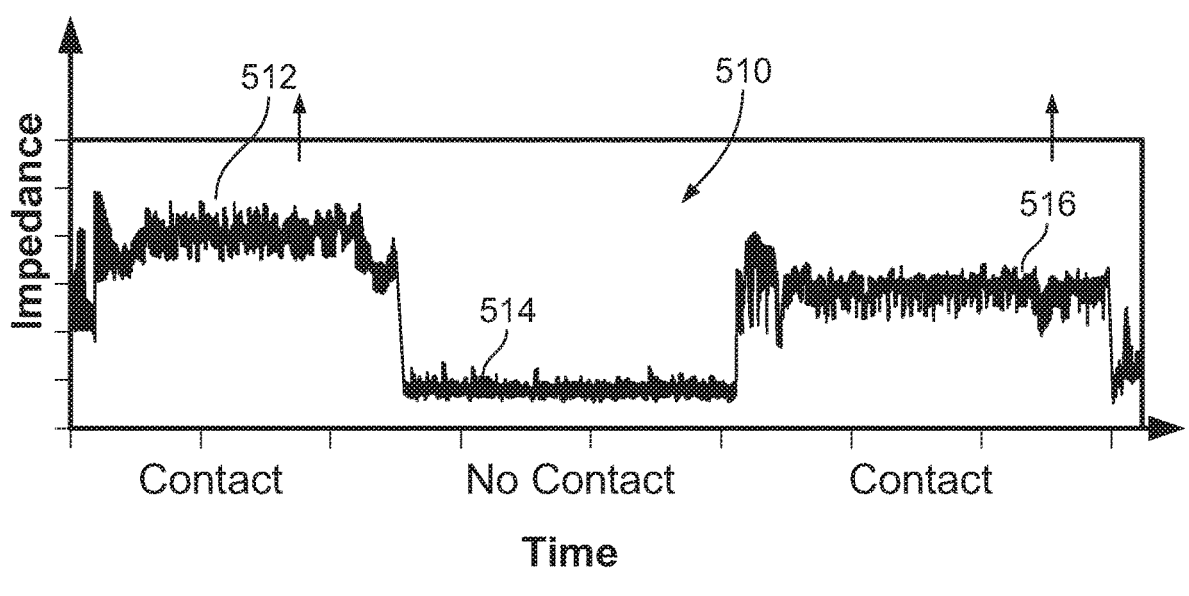
FIG. 11 is a graph of electrical activity indicative of position of the distal section of the catheter relative to the tissue, according to an embodiment of the present invention.

FIG. 11 is a graph showing a curve/signal 510 representative of electrical activity (e.g., resistance) arising from manually manipulating a cryoablation catheter similar to that described above with respect to FIG. 10 in use in porcine cardiac tissue in blood. The catheter was initially placed in contact with right atrial tissue, then it was moved so it was entirely floating in blood (no tissue contact), then again it was placed into contact with tissue. The positioning of the catheter was verified by fluoroscopy.

The curve/signal 510 includes peak 512, valley 514, and peak 516. Peaks 512, 514 of higher activity correspond to the applicable electrode region being placed in contact with the target tissue. Valley 514 corresponds to the catheter not making contact with the tissue. Peaks and valleys 510, 512 and 514 were measured form the same electrode pair that was moved into and out of contact with tissue. Without being bound by theory, this phenomena arises because tissue has a higher resistance than blood. When the current is sent through the tissue from one electrode to another, the resistance is higher than that of blood. This is reflected in peaks 512, 516.

In embodiments, reactance to the current sent through the tissue is monitored and impedance is computed. Impedance is defined in rectangular coordinates as $Z=R+jX$, where R is resistance, and jX is the reactance component. In embodiments, the impedance components (e.g., resistance and reactance) are separately measured and evaluated. In embodiments, a total impendence is monitored without separating out the individual components. While the above described circuit or system may be used to evaluate impendence the invention is not so limited. Other systems and circuits for generating and processing the current and signals may be incorporated into the present invention. Additional examples of circuits for measuring electrical activity are described in U.S. Pat. No. 8,449,535 to Deno et al.

In embodiments tissue contact may be confirmed, cryoablation performed, and treatment efficacy determined, with all steps carried out without repositioning the electrodes.

Many modifications and variations of the present invention are possible in light of the above teachings. It is, therefore, to be understood that within the scope of the appended claims, the invention may be practiced otherwise than as specifically described.

We claim:

1. A cryoablation system for creating a lesion in tissue, comprising:
   a catheter comprising a flexible body and a distal treatment section, wherein the distal treatment section is adjustable from a substantially linear configuration to a curved configuration;
   a plurality of electrodes on the distal treatment section; and
   a console comprising a processor programmed to:
   a) commence and terminate circulation of a cryogenic fluid through the distal treatment section for creating the lesion in the tissue;
   b) monitor electrical activity from the plurality of electrodes on the distal treatment section;
   c) calculate a tissue-contact value indicative of a length of the distal treatment section in direct contact with the tissue, based on the monitored electrical activity;
   d) compute tissue freezing during circulation of the cryogenic fluid and tissue thawing based on the monitored electrical activity; and
   e) confirm tissue necrosis subsequent to confirming tissue freezing based on the monitored electrical activity and
   wherein the processor is further programmed to compute tissue thawing by comparing noise from the electrical activity to a threshold value.

2. The system of claim 1, wherein the console is configured to receive electrocardiogram (ECG) signals based on the plurality of electrodes on the distal treatment section.

3. The system of claim 2, wherein confirming tissue necrosis comprises comparing a pre-freeze ECG signal to a post-freeze ECG signal.

4. The system of claim 1, wherein the console is further configured to send a current to at least one of the plurality of electrodes, and to acquire a total impedance value from the monitored electrical activity.

5. The system of claim 1, wherein the console is further configured to send the tissue-contact value to a display.

6. The system of claim 1, wherein the console is further configured to compute an image or beacon of the distal treatment section in direct contact with the target tissue.

7. The system of claim 1, wherein the step of confirming necrosis comprises confirming pulmonary vein isolation.

8. The system of claim 1, wherein the step of confirming necrosis comprises confirming cavo-tricuspid isthmus (CTI) bidirectional block.

9. The system of claim 1, wherein the processor is further programmed to confirm whether the catheter is safe to move based on the monitored electrical activity.

10. The system of claim 1, wherein the tissue comprises cardiac tissue.

11. The system of claim 1, wherein the at least one electrode is formed of a continuous/junction-free electrically conducting material.

12. The system of claim 1, wherein the at least one electrode is a band.

13. The system of claim 1, wherein the at least one electrode is a plurality of pairs of electrodes.

14. The system of claim 1, wherein the at least one electrode is at least one pair of electrodes for bipolar recording of electrical activity.

15. The system of claim 1, wherein the distal treatment section is adjustable to form a line, ring or oval shape.

16. The system of claim 1, wherein the electrical activity arises free of the Seebeck effect.

17. The system of claim 1, wherein the cryogenic fluid is Nitrogen.

* * * * *